United States Patent [19]

Grasshoff et al.

[11] Patent Number: 5,453,345
[45] Date of Patent: Sep. 26, 1995

[54] IMAGING MEDIUM

[75] Inventors: Jurgen M. Grasshoff, Hudson; John L. Marshall, Somerville; Richard A. Minns, Arlington; Anthony J. Puttick, Arlington; Lloyd D. Taylor, Lexington; Stephen J. Telfer, Arlington, all of Mass.

[73] Assignee: Polaroid Corporation, Cambridge, Mass.

[21] Appl. No.: 141,852

[22] Filed: Oct. 22, 1993

Related U.S. Application Data

[63] Continuation-in-part of Ser. No. 965,161, Oct. 23, 1992, Pat. No. 5,286,612.

[51] Int. Cl.[6] .................... G03C 1/492; G03C 1/494; G03C 1/76
[52] U.S. Cl. .................... 430/270; 430/340; 430/944; 430/945
[58] Field of Search .................... 430/270, 335, 430/944, 945, 333, 336, 340, 346, 269, 203; 549/331, 332; 204/157.45

[56] References Cited

U.S. PATENT DOCUMENTS

| | | | |
|---|---|---|---|
| 3,617,270 | 11/1971 | Kampfer | 430/62 |
| 3,915,706 | 10/1975 | Limburg et al. | 96/27 R |
| 3,932,514 | 1/1976 | Thelen et al. | 260/586 P |
| 4,092,146 | 5/1978 | Fischer et al. | 71/70 |
| 4,159,387 | 6/1979 | Bellus | 560/185 |
| 4,345,017 | 8/1982 | Cournoyer et al. | 430/221 |
| 4,508,811 | 4/1985 | Gravesteijn et al. | 430/270 |
| 4,602,263 | 7/1986 | Borrer et al. | 346/201 |
| 4,678,737 | 7/1987 | Schneller et al. | 430/270 |
| 4,720,449 | 1/1988 | Borrer et al. | 430/338 |
| 4,826,976 | 5/1989 | Borrer et al. | 544/58.4 |
| 4,857,437 | 8/1989 | Banks et al. | 430/270 |
| 4,916,046 | 4/1990 | Doessel | 430/281 |
| 4,992,571 | 2/1991 | Fukuyama et al. | 566/64 |
| 5,037,575 | 8/1991 | Miura et al. | 430/70 |
| 5,055,376 | 10/1991 | Saeva | 430/270 |
| 5,084,371 | 1/1992 | Schwalm et al. | 430/270 |
| 5,102,771 | 4/1992 | Vogel et al. | 430/270 |
| 5,141,969 | 8/1992 | Saeva et al. | 430/270 |
| 5,227,498 | 7/1993 | Lee et al. | 549/404 |
| 5,227,499 | 7/1993 | McGowan et al. | 549/404 |

FOREIGN PATENT DOCUMENTS

| | | |
|---|---|---|
| 824630 | 10/1969 | Canada. |
| WO92/09661 | 6/1992 | WIPO. |

OTHER PUBLICATIONS

Berry et al., Chemically Amplified Resists for I–line and G–line Applications, SPIE 1262, 575 (1990).
Bou et al., Tetrahedron Letters, 23(3), 361(1982).
Cohen S. and Cohen, S. G., J. Am. Chem. Soc., 88, 1533 (1966).
Crivello et al., J. Polym. Sci., Polym. Chem. Ed., 16, 2441 (1978).
Dehmlow et al., Chem. Ber. 113(1), 1–8 (1979).
Dehmlow et al., Chem. Ber. 121(3), 569–71 (1988).
Islam, N. et al., Tetrahedron 43, 959–970 (1987).
Pericas et al., Tetrahedron Letters, (1977), 4437–38.
Reichmanis et al., Chemical Amplification Mechanism for Microlithography, Chem. Mater., 3(3), 394 (1991).

*Primary Examiner*—Charles L. Bowers, Jr.
*Assistant Examiner*—Geraldine Letscher
*Attorney, Agent, or Firm*—David J. Cole

[57] ABSTRACT

Acid can be generated by exposing a mixture of a superacid precursor and a dye to actinic radiation of a first wavelength which does not, in the absence of the dye, cause decomposition of the superacid precursor to form the corresponding superacid, thereby causing absorption of the actinic radiation and decomposition of part of the superacid precursor, with formation of a protonated product derived from the dye, then irradiating the mixture with actinic radiation of a second wavelength, thereby causing decomposition of part of the remaining superacid precursor, with formation of unbuffered superacid. Preferably, following these irradiations, the imaging medium is heated while the superacid is admixed with a secondary acid generator capable of being thermally decomposed to form a second acid, the thermal decomposition of the secondary acid generator being catalyzed by the presence of the superacid. The acid generation process may be used for imaging by bringing the superacid or second acid into contact with an acid-sensitive material which changes color on contact with acid, or the superacid may be used to trigger polymerization, depolymerization or other reactions.

16 Claims, 4 Drawing Sheets

IMAGING MEDIUM

REFERENCE TO PARENT APPLICATION

This application is a continuation-in-part of application Ser. No. 07/965,161, filed Oct. 23, 1992, now U.S. Pat. No. 5,286,612.

REFERENCE TO RELATED APPLICATIONS AND PATENTS

Attention is directed to copending application Ser. No. 07/965,172, and its divisional application Ser. No. 08/106,353, filed Aug. 13, 1993; these two applications describe and claim a process and imaging medium generally similar to those of the present invention, but in which the breakdown of a squaric acid derivative is initiated thermally.

Attention is also directed to copending application Ser. No. 07/965,162 (now U.S. Pat. No. 5,286,612) and its continuation-in-part, application Ser. No. 08/141,866 now U.S. Pat. No. 5,346,736, of even date herewith and assigned to the same assignee as the present application; these two applications describe and claim a process and imaging medium generally similar to those of the present invention but in which a superacid precursor is exposed to actinic radiation effective to generate superacid from the superacid precursor, and the resultant superacid is heated while admixed with a secondary acid generator (typically a squaric acid derivative or an oxalate) capable of thermally decomposing to produce an acid, thereby causing production of a secondary acid.

Finally, attention is directed to copending application Ser. No. 08/084,759, filed Sep. 17, 1993 and assigned to the same assignee as the present application; this application describes and claims a process and imaging medium using a mixture of a diaryl iodonium salt and a squarylium dye capable of absorbing infra-red radiation having a wavelength within the range of about 700 to about 1200 nm, the dye having a squarylium ring the 1- and 3-positions of which are each connected, via a single $Sp^2$ carbon atom, to a pyrylium, thiopyrylium, benzpyrylium or benzthiopyrylium moiety, at least one of the $Sp^2$ carbon atoms having a hydrogen atom attached thereto, and the 2-position of the squarylium ring bearing an $O^-$, amino or substituted amino, or sulfonamido group. The mixture is irradiated with infra-red radiation having a wavelength within the range of about 700 to about 1200 nm, thereby causing absorption of the radiation by the squarylium dye and formation of acid in the mixture.

BACKGROUND OF THE INVENTION

This invention relates to a process for generation of acid and for imaging, and to an imaging medium for use in this imaging process.

Some conventional non-silver halide photosensitive compositions, for example photoresists, contain molecules which are inherently photosensitive, so that absorption of a single photon brings about decomposition of only the single molecule which absorbs the photon. However, a dramatic increase in the sensitivity of such photosensitive compositions can be achieved if the photosensitive molecule initiates a secondary reaction which is not radiation-dependent and which effects conversion of a plurality of molecules for each photon absorbed. For example, photoresist systems are known in which the primary photochemical reaction produces an acid, and this acid is employed to eliminate acid-labile groups in a secondary, radiation-independent reaction. See, for example, U.S. Pat. Nos. 3,932,514 and 3,915,706; Reichmanis et al., Chemical Amplification Mechanism for Microlithography, Chem. Mater.,3(3), 394 (1991) and Berry et al., Chemically Amplified Resists for I-line and G-line Applications, SPIE, 1262, 575 (1990). Also, U.S. Pat. No. 5,084,371 describes a radiation-sensitive mixture which contains a water-insoluble binder which comprises a mixture of phenolic and novolak polymers and which is soluble or dispersible in aqueous alkali, and an organic compound whose solubility in alkaline developer is increased by acid, and which also contains at least one acid-cleavable group, and in addition a further group which produces a strong acid upon exposure to radiation.

U.S. Pat. No. 4,916,046 describes a positive radiation-sensitive mixture using a monomeric silylenol ether, and a recording medium produced therefrom. This patent also contains an extensive discussion of radiation-sensitive compositions which form or eliminate an acid on irradiation. According to this patent, such radiation-sensitive compositions include diazonium, phosphonium, sulfonium and iodonium salts, generally employed in the form of their organic solvent-soluble salts, usually as deposition products with complex acids such as tetrafluoroboric acid, hexafluorophosphoric acid, hexafluoroantimonic acid and hexafluoroarsenic acid; halogen compounds, in particular triazine derivatives; oxazoles, oxadiazoles, thiazoles or 2-pyrones which contain trichloromethyl or tribromomethyl groups; aromatic compounds which contain ring-bound halogen, preferably bromine; a combination of a thiazole with 2-benzoylmethylenenaphthol; a mixture of a trihalomethyl compound with N-phenylacridone; α-halocarboxamides; and tribromomethyl phenyl sulfones.

The aforementioned phosphonium, sulfonium and iodonium salts are superacid precursors which, upon exposure to ultraviolet radiation, decompose to produce superacids, that is to say acids with a $pK_a$ less than about 0. Other materials decompose to produce superacids in a similar manner. However, all the superacid precursors require ultraviolet to blue visible radiation for decomposition (see, for example, Crivello and Lam, Dye-Sensitized Photoinitiated Cationic Polymerization, J. Polymer Sci., 16, 2441 (1978)), and the need for this radiation is disadvantageous when it is desired to produce high resolution images, which are most conveniently produced by laser imaging. In the present state of technology, diode lasers emitting at near infra-red wavelengths of about 700 to 1200 nm. provide the highest output per unit cost. Near infra-red solid state lasers emitting at about 1000–1200 nm. are also useful in imaging processes, while ultraviolet lasers are costly. Accordingly, it is desirable to find some way in which superacid precursors can be rendered susceptible to infra-red radiation in order that imaging of a superacid precursor-containing medium can be effected using an infra-red laser.

It is already known that various sensitizing dyes can catalyze the decomposition of superacid precursors upon exposure to wavelengths to which the superacid precursors are not sensitive in the absence of the sensitizing dye. Unfortunately, due to the difficulty of protonating the superacid anion consequent upon the very low $pK_a$ of the superacid, the sensitizing dye is protonated by the superacid, so that no unbuffered superacid is produced in the medium (i.e., the sensitizing dye buffers the superacid produced). Since no unbuffered superacid is released into the medium, these processes cannot be used to trigger any secondary reaction which requires the presence of unbuffered strong acid, such as the reactions used in many photoresists, as described in the aforementioned patents.

(The term "unbuffered superacid" is used herein to refer to superacid which is not buffered by the sensitizing dye, and which thus provides an acidic species stronger than that provided by buffered superacid, that is to say superacid buffered by the sensitizing dye. Because of the extreme acidity of superacids and their consequent tendency to protonate even species which are not normally regarded as basic, it is possible, and indeed likely, that "unbuffered superacid" will in fact be present as a species buffered by some component of the imaging medium less basic than the sensitizing dye. However, such buffering by other species may be ignored for present purposes, so long as superacid is present as an acidic species stronger than that provided by superacid buffered by the sensitizing dye.)

This invention provides a process for generation of acid which enables a medium containing a superacid precursor and a sensitizing dye, which is more easily protonated than the superacid anion, to be imaged with radiation of a frequency to which the superacid precursor is not sensitive, so as to produce unbuffered superacid in the medium. By including an acid-sensitive material in the medium, the process can be used for imaging.

SUMMARY OF THE INVENTION

Accordingly, this invention provides a process for generation of acid, which process comprises:

providing a medium containing a mixture of a superacid precursor and a dye capable of absorbing actinic radiation of a first wavelength which does not, in the absence of the dye, cause decomposition of the superacid precursor to form the corresponding superacid, the superacid precursor being capable of being decomposed by actinic radiation of a second wavelength shorter than the first wavelength;

irradiating the medium with actinic radiation of the first wavelength, thereby causing absorption of the actinic radiation, and decomposition of part of the superacid precursor, without formation of unbuffered superacid but with formation of a protonated product derived from the dye; and thereafter irradiating the medium with actinic radiation of the second wavelength, thereby causing decomposition of part of the remaining superacid precursor, with formation of unbuffered superacid.

In a preferred form of this process, only part of the medium is irradiated with the actinic radiation of the first wavelength, but a larger portion of the medium is irradiated with the actinic radiation of the second wavelength, such that unbuffered superacid is generated in the part of the medium exposed to the radiation of both the first and second wavelengths, but no unbuffered superacid is generated in the part of the medium exposed to the radiation of the second wavelength but not to the radiation of the first wavelength. Desirably, the medium is imagewise exposed to the actinic radiation of the first wavelength so that the unbuffered superacid generated forms an image.

This invention also provides an imaging medium comprising:

a superacid precursor; and a dye capable of absorbing actinic radiation of a first wavelength, the superacid precursor being decomposed to form a superacid by actinic radiation of a second wavelength shorter than the first wavelength, but not being decomposed by actinic radiation of the first wavelength in the absence of the dye, the superacid produced by decomposition of the superacid precursor being capable of forming a protonated product derived from the dye; and a secondary acid generator capable of being thermally decomposed to form a second acid, the thermal decomposition of the secondary acid generator being catalyzed in the presence of the superacid.

Finally, this invention provides an imaging medium comprising:

a superacid precursor and an infra-red dye capable of absorbing infrared radiation having a wavelength within the range of about 700 to about 1200 nm, the superacid precursor being capable of being decomposed by ultraviolet radiation having a wavelength in the range of about 180 to about 400 nm to form a superacid, the superacid precursor not being decomposed by infra-red radiation having a wavelength within the range of about 700 to about 1200 nm in the absence of the infra-red dye.

DETAILED DESCRIPTION OF THE INVENTION

Figure 1A:
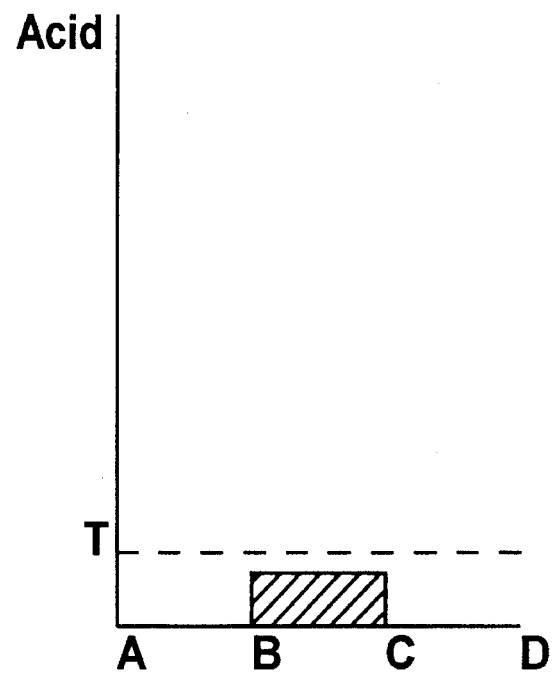
FIGS. 1 A–1D show the acid concentrations in the exposed and unexposed regions of the imaging medium during the various steps of a preferred process of the present invention.

As already mentioned, the present process employs a medium containing a mixture of a superacid precursor and a dye. The dye (which may hereinafter be referred to as the "sensitizing dye") is capable of absorbing actinic radiation of a first wavelength which does not, in the absence of the sensitizing dye, cause decomposition of the superacid precursor to form the corresponding superacid; typically this first wavelength is in the range of about 700 to about 1200 nm, so that the sensitizing dye is a near infra-red dye. Also, the superacid precursor is capable of being decomposed by actinic radiation of a second wavelength shorter than the first wavelength; typically this second wavelength is in the range of about 400 to about 180 nm, so that the actinic radiation of the second wavelength can be conveniently supplied by ultraviolet sources (e.g., a mercury arc lamp) which are readily available and will be familiar to those skilled in the art.

As is well known to those familiar with superacid precursors, superacid precursors may require the presence of a precursor sensitizer, typically a polycyclic hydrocarbon such as pyrene, to enable the superacid precursor to break down upon irradiation with ultraviolet or other actinic radiation, thereby producing superacid. Accordingly, references herein to a superacid precursor shall be construed to refer to a mixture of superacid precursor and precursor sensitizer, if the superacid precursor is one which requires the presence of such a precursor sensitizer.

The medium is first irradiated with actinic radiation of the first wavelength, thereby causing absorption of the actinic radiation and decomposition of part of the superacid precursor, with formation of a protonated product derived from the dye. Thereafter, the medium is irradiated with actinic radiation of the second wavelength, thereby causing decomposition of part of the remaining superacid precursor, with formation of unbuffered superacid.

Since the purpose of the present invention is to produce unbuffered superacid, which may be used for various purposes as discussed below, it is highly desirable that the process be conducted under essentially anhydrous conditions; as chemists are well aware, the most powerful acidic species which can exist in the presence of more than one equivalent of water is the hydroxonium (hydronium) ion, $[H_3O]^+$. Accordingly, if the medium in which the present process is conducted contains water, at least part of the superacid produced by the present process will simply generate hydroxonium ion. However, in the absence of water, the superacid yields an acidic species much stronger than hydroxonium ion, and this acidic species can be used for purposes for which hydroxonium ion cannot, for example the acid-catalyzed decomposition of various secondary acid generators, as discussed in detail below. Typically, the present process is carried out with the superacid precursor and the dye dispersed in a polymeric binder, and such binders can readily be chosen to provide an essentially anhydrous environment for the process.

For the present process to occur, it is necessary that the sensitizing dye, having absorbed the radiation of the first wavelength, be capable of initiating the decomposition of the superacid precursor. As is well-known to those skilled in the art, for such initiation to occur, it is necessary to choose the sensitizing dye and the superacid precursor so that the excited state of the sensitizing dye is capable of reducing the superacid precursor. The choice of appropriate pairs of sensitizing dyes and superacid precursors may be made empirically, although techniques familiar to those skilled in the art, such as use of the Rehm-Weller Equation, may be used to reduce the amount of empirical testing necessary.

As already noted, in a preferred form of the process, only part of the medium is irradiated with the actinic radiation of the first wavelength but a larger portion of the medium is irradiated with the actinic radiation of the second wavelength, such that unbuffered superacid is generated in the part of the medium exposed to the radiation of both the first and second wavelengths, but no unbuffered superacid is generated in the part of the medium exposed to the radiation of the second wavelength but not to the radiation of the first wavelength. Desirably, the medium is imagewise exposed to the actinic radiation of the first wavelength so that the unbuffered superacid generated in the exposed areas of the medium forms a latent "image" in acid; this image is not necessarily visible to the unaided human eye but may be converted to a visible or otherwise useful image (e.g., a printing plate) as described below.

The superacid produced by the present process may be used to carry out any of the reactions which have hitherto been carried out using superacid generated by prior art processes. For example, the imaging medium may comprise a monomer or oligomer which polymerizes in the presence of the unbuffered superacid. If such a medium is imagewise exposed by the present process, in the part of the medium exposed to the radiation of both the first and second wavelengths, the monomer or oligomer polymerizes, but in the part of the medium not exposed to the radiation of the first wavelength, the monomer remains substantially unpolymerized. Alternatively, the imaging medium may comprise a polymer which depolymerizes in the presence of the unbuffered superacid. When such a medium is imagewise exposed by the present process, in the part of the medium exposed to the radiation of both the first and second wavelengths, the polymer depolymerizes, but in the part of the medium not exposed to the radiation of the first wavelength, the polymer remains substantially polymerized. The imaging medium may also comprise a polymer the solubility of which in a solvent changes in the presence of unbuffered superacid. Following exposure of the medium to the radiation of both the first and second wavelengths, the medium is treated with the solvent, whereby the polymer is removed from one of the exposed and unexposed areas of the medium (i.e., the areas of the medium exposed and not exposed respectively to the radiation of the first wavelength), but is not removed from the other of these areas. Thus, any of these types of imaging medium can act as a photoresist.

A further form of the present imaging medium comprises a polymer the adhesion of which to a material changes in the presence of the unbuffered superacid. Following exposure of the medium to the radiation of both the first and second wavelengths, the polymer is contacted with this material, so that either the exposed or the unexposed areas of the medium adheres to the material, while the other of these areas does not adhere. For example, the present imaging medium may comprise a substrate in contact with one face of the layer(s) containing the imaging components (i.e., the superacid precursor, sensitizing dye and polymer), and a topcoat on the opposed side of the layer(s) containing the imaging components. The polymer is chosen (for example) so that before exposure to unbuffered superacid it adheres more strongly, whereas after exposure to unbuffered superacid it adheres less strongly to the substrate than to the topcoat. After imagewise exposure of the medium to the radiation of the first and second wavelengths and, optionally, heating, the substrate and topcoat are peeled away from one another. In unexposed areas, the polymer remains more adherent to the substrate than to the topcoat, and remains with the substrate, whereas in exposed areas, the polymer adheres less strongly to the substrate than to the topcoat, and consequently remains with the topcoat. Thus, upon peeling, the polymer-containing layer will fracture, with the unexposed parts remaining on the substrate and the exposed parts being removed with the topcoat.

Alternatively, the material with which the polymer is brought into contact after exposure can be a pulverulent material, for example a toning powder. An imaging medium of this type may comprise a polymer which is essentially non-tacky prior to exposure but which becomes tacky after exposure. After exposure, the toning powder is spread over the imaging medium, and adheres only to the exposed areas of polymer. Excess toning powder may then be removed, for example by blowing air across the imaging medium, thus leaving a visible image formed by the toning powder adhering only to the exposed areas of the imaging medium.

In another type of imaging medium of the present invention, the quantity of acid generated in the medium by the present process is increased ("amplified") by heating the medium, following the irradiation with the actinic radiation of the second wavelength, while the superacid is admixed with a secondary acid generator capable of superacid-catalyzed decomposition to form a second acid, the thermal decomposition of the acid generator being catalyzed by the presence of the superacid. When such an imaging medium is imagewise exposed to actinic radiation of the first wavelength, in the part of the medium irradiated with the actinic radiation of the first wavelength, the superacid catalyzes the decomposition of the secondary acid generator and the second acid is formed, whereas the part of the medium not irradiated with the actinic radiation of the first wavelength remains essentially free from the second acid.

The chemical changes which occur in exposed and unexposed regions of a preferred imaging medium of the present invention are shown in Table 1 below, while the corresponding changes in acid concentration in exposed and unexposed areas are shown in FIGS. 1A–1D.

TABLE 1

| EXPOSED AREA | | UNEXPOSED AREA | |
|---|---|---|---|
| Component | Moles | Component | Moles |
| PRIOR TO EXPOSURE | | | |
| [DYE] | 1 | [DYE] | 1 |
| Secondary acid generator | 10 | Secondary acid generator | 10 |
| $Ph_2I^+PF_6^-$ | 5 | $Ph_2I^+PF_6^-$ | 5 |
| AFTER IMAGEWISE INFRA-RED EXPOSURE | | | |
| $Ph$-$[DYE$-$H]^+PhIPF_6^-$ | 0.75 | [DYE] | 1 |
| [DYE] | 0.25 | Secondary acid generator | 10 |
| Secondary acid generator | 10 | | |
| $Ph_2I^+PF_6^-$ | 4.25 | $Ph_2I^+PF_6^-$ | 5 |
| AFTER BLANKET ULTRA-VIOLET EXPOSURE | | | |
| $Ph$-$[DYE$-$H]^+PhIPF_6^-$ | 0.75 | [DYE] | 0.25 |
| $[DYE$-$H]^+PF_6^-$ | 0.25 | $[DYE$-$H]^+PF_6^-$ | 0.75 |
| $HPF_6$ | 0.5 | Secondary acid generator | 10 |
| Secondary acid generator | 10 | | |
| $Ph_2I^+PF_6^-$ | 3.5 | $Ph_2I^+PF_6^-$ | 4.25 |
| AFTER HEATING | | | |
| $Ph$-$[DYE$-$H]^+PhIPF_6^-$ | 0.75 | [DYE] | 0.25 |
| $[DYE$-$H]^+PF_6^-$ | 0.25 | $[DYE$-$H]^+PF_6^-$ | 0.75 |
| $HPF_6$ | 0.5 | Secondary acid generator | 10 |
| Second acid | 10 | | |
| $Ph_2I^+PF_6^-$ | 3.5 | $Ph_2I^+PF_6^-$ | 4.25 |
| AFTER BASE ADDITION | | | |
| $Ph$-$[DYE$-$H]^+PhIPF_6^-$ | 0.75 | [DYE] | 1 |
| $[DYE$-$H]^+PF_6^-$ | 0.25 | $[BASE$-$H]^+PF_6^-$ | 0.75 |
| $[BASE$-$H]^+PF_6^-$ | 0.5 | Secondary acid generator | 10 |
| Second acid | 9 | | |
| Base/second acid salt | 1 | $Ph_2I^+PF_6^-$ | 4.25 |
| $Ph_2I^+PF_6^-$ | 3.5 | | |

As shown in Table 1, prior to exposure both the exposed and unexposed regions comprise a quantity (shown in Table 1 as 1 mole for simplicity; all references to moles concerning Table 1 refer to moles per unit area of the imaging medium) of an infra-red sensitizing dye, a larger molar quantity of a superacid precursor (5 moles of $Ph_2I^{30}$ $PF_6^-$ are shown in Table 1; a suitable quantity of a precursor sensitizer, such as pyrene, is also included in the medium but is not shown in Table 1) and a still larger molar quantity (10 moles are shown in Table 1) of a secondary acid generator.

The imaging medium is first imagewise irradiated with infra-red radiation of a frequency absorbed by the sensitizing dye, the amount of radiation applied being sufficient to cause the infra-red dye to bring about decomposition of less than one mole (0.75 mole is used for illustration in Table 1 and FIG. 1) of the superacid precursor. In the area of the imaging medium exposed to the infra-red radiation (hereinafter referred to as the "exposed area"), upon absorbing the infra-red radiation, the sensitizing dye transfers an electron to the superacid precursor, which then fragments to produce a phenyl radical and phenyl iodide. Although the secondary reactions which follow this fragmentation of the superacid precursor are not entirely understood at present, one pathway for further reaction may be combination of a radical cation derived from the sensitizing dye with the phenyl radical derived from the superacid precursor, and subsequent loss of a proton from the sensitizing dye to form a protonated species derived from the sensitizing dye and designated "Ph-[DYE-H]" in Table 1, with charge balancing being effected by an anion derived from the superacid precursor. Each sensitizing dye molecule transfers only a single electron, and hence generates a single proton, before being converted to the protonated species, and this protonated species does not carry out the electron transfer reaction. Hence, since each sensitizing dye molecule brings about breakdown of only a single molecule of superacid precursor before being deactivated, the sensitizing dye will not bring about decomposition of a greater molar quantity of the superacid precursor than the molar quantity of sensitizing dye originally present, and the superacid generated is completely buffered by the dye. Hence, following the infra-red exposure, no unbuffered superacid is present in the exposed area. At this stage, the secondary acid generator in the exposed area remains unchanged. In the unexposed area, the infra-red irradiation effects no change in any of the components of the imaging medium.

The acid concentrations in the exposed and unexposed regions following this first step of the process are shown schematically in FIG. 1A, in which acid concentration is plotted along a line across the medium in which section BC is in an exposed area, while sections AB and CD are in unexposed areas. As shown in FIG. 1A, following the first step of the process, no acid is present in unexposed areas AB and CD, while the level of acid present in exposed area BC is below a threshold level T, which represents the level of acid which can be buffered by the sensitizing dye; theoretically, the level of acid in area BC should be 0.75 T. Hence, as already stated, all of the acid present in exposed area BC is buffered by the sensitizing dye, and the imaging medium contains 0.75 mole of the Ph-[DYE-H]$^+$ and no unbuffered superacid.

Figure 1B:
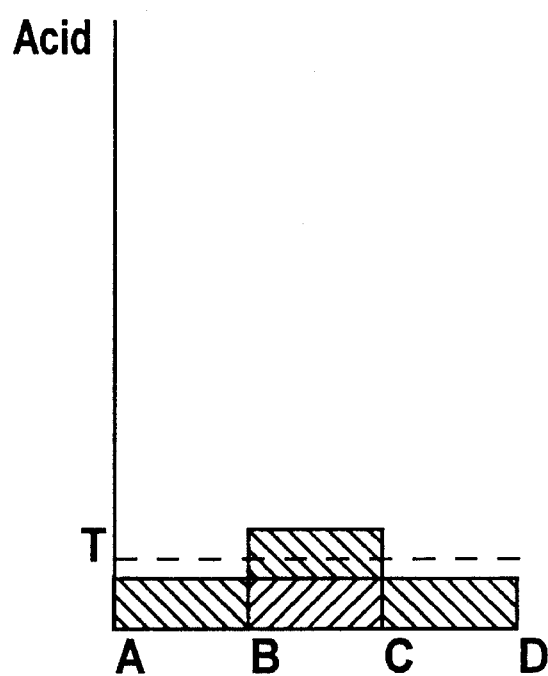

In the next stage of the imaging process, the whole of the imaging medium is irradiated with ultraviolet radiation effective to cause breakdown of the superacid precursor, with generation of unbuffered superacid. The amount of ultraviolet radiation irradiated is chosen so as to produce a molar amount of superacid less than the molar amount of dye present in the unexposed medium, and in Table 1 is shown as sufficient to produce 0.75 mole of superacid. As illustrated in Table 1 and FIG. 1B, in the exposed area BC of the imaging medium (i.e., in the area exposed to the infra-red radiation), the additional 0.75 mole of superacid generated by the ultra-violet exposure, combined with the 0.75 mole generated by the infra-red exposure, exceeds the threshold level T, and thus protonates all the sensitizing dye present and leaves additional superacid in unbuffered form. (For purposes of illustration, FIG. 1B shows the acid generated in the infra-red and ultra-violet exposures separately, although of course no difference exists chemically.) In the unexposed areas AB and CD, on the other hand, only the 0.75 mole of superacid generated by the ultra-violet exposure is present, the acid concentration remains below the threshold level T, and all of the superacid produced is buffered by the sensitizing dye, so that no unbuffered superacid is present following the ultraviolet irradiation. (As shown in Table 1, the buffered complex formed by the sensitizing dye and the superacid precursor in the unexposed areas AB and CD during the ultraviolet irradiation differs from that produced in the exposed area BC during the infra-red irradiation. During the ultraviolet irradiation, the superacid precursor typically transfers a phenyl group not to the dye but rather to the precursor sensitizer (which is effectively non-basic), so that only a proton comes to reside on the infra-red sensitizing dye. However, this difference between the two buffered complexes does not affect the present process, since both complexes efficiently buffer the superacid.)

Thus, at the end of the blanket ultraviolet irradiation, unbuffered superacid is present in the exposed area, whereas in the unexposed area no unbuffered superacid is present, all the superacid generated being buffered by the sensitizing dye.

The two steps already described may be the only steps of the present process. If, for example, the present process is to be used to bring about polymerization of a monomer or oligomer, or depolymerization of a polymer, the unbuffered superacid produced in area BC in FIG. 1B may be used directly to carry out the desired polymerization or depolymerization. It will be appreciated that, in such polymerization or depolymerization processes, the secondary acid generator can be omitted from the imaging medium.

Figure 1C:
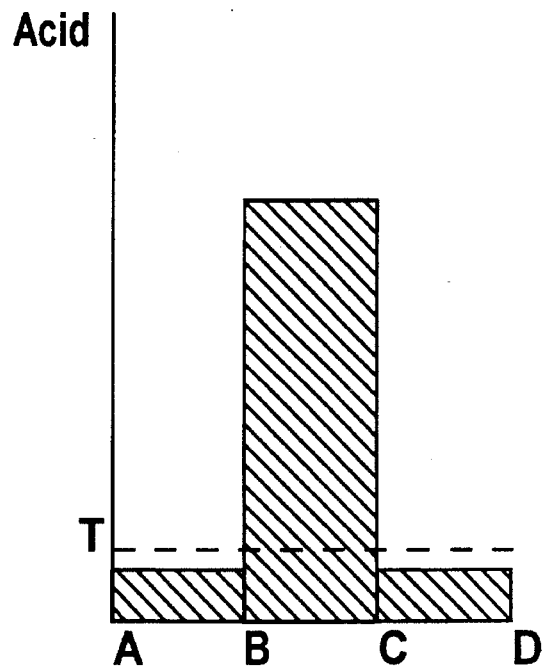
Figure 1D:
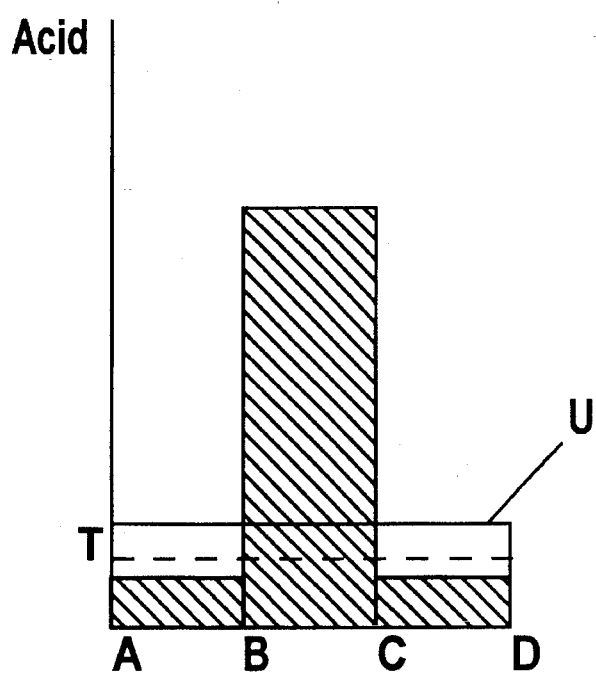

However, in a preferred process of the invention, the imaging medium is next heated. In the exposed area BC, the unbuffered superacid present catalyzes the decomposition of the secondary acid generator, thereby producing a large quantity of the second acid (10 moles are shown by way of example in Table 1; FIG. 1C is not strictly to scale). However, in the unexposed areas AB and CD, no unbuffered superacid is present, and the dye-superacid complex does not catalyze the decomposition of the secondary acid generator, so that essentially no decomposition of the secondary acid generator occurs and essentially no second acid is generated.

In the final step of the preferred process, as discussed in more detail below, a quantity of base is introduced into the imaging medium; 1.5 moles of base are shown in Table 1. The effect of this addition of base is to reduce acid levels throughout the imaging medium, as indicated by the box U in FIG. 1D. The addition of this base serves to ensure that, if a small amount of uncatalyzed thermal decomposition of the secondary acid generator does occur in unexposed areas AB and CD during the heating step, the small amount of second acid resulting will be neutralized by base before the second acid can effect changes in an acid-sensitive material, as described in more detail below. Although the addition of the base does reduce the amount of free acid present in the exposed area BC, this reduction is not significant since a more than adequate amount of second acid remains in the exposed area BC to affect an acid-sensitive material. The addition of base to the unexposed areas AB and CD leaves a surplus of base in these areas and thus serves to ensure that, if minor decomposition of the superacid precursor does occur after the present process has been completed, the minor amounts of superacid generated will be neutralized by the base and thus will not affect acid-sensitive material present in these unexposed areas.

From the foregoing description, it will be seen that, in the exposed area, the superacid catalyzes the breakdown of the secondary acid generator, so that the final quantity of second acid present is substantially larger than the quantity of superacid produced directly by the actinic radiation acting on the superacid precursor, although of course the secondary acid is typically a weaker acid than the superacid itself. This "chemical amplification" of the superacid by the secondary acid generator increases the number of moles of acid generated per einstein of radiation absorbed, and thus increases the contrast of the image produced by the present process as compared with simple generation of superacid by a superacid precursor. In practice, it has been found that, under proper conditions, at least 20 moles of second acid can be liberated for each mole of unbuffered superacid present in the exposed areas following the ultra-violet irradiation.

One of the advantages of the present process is that, at least in many preferred embodiments of the invention, it is possible to compensate for any premature breakdown of the superacid precursor which may occur prior to use of the imaging medium, for example as a result of exposure of the imaging medium to ambient infra-red or ultra-violet radiation during transportation and storage or because the combination of the superacid precursor and the sensitizing dye undergoes slow decomposition on protracted storage. With most infra-red sensitizing dyes, the protonated products derived from the sensitizing dye will absorb at a wavelength significantly different from the unprotonated sensitizing dye, so that it will be possible to differentiate between the unprotonated dye and protonated product by measuring absorption at an appropriate infra-red wavelength. The amount of infra-red and ultra-violet irradiation can be adjusted to ensure that the present process works properly even if some decomposition of the superacid precursor has taken place prior to use of the medium.

For example, to take an extreme case purely for purposes of illustration, suppose that the imaging medium shown in Table 1 is exposed to so much infra-red radiation during storage and transit that half of the infra-red sensitizing dye has already been converted to the Ph-[DYE-H]$^+$ form prior to use, with corresponding breakdown of 0.5 mole of superacid precursor, so that in all areas the medium initially contains 0.5 mole of sensitizing dye, 10 moles of secondary acid generator, 4.5 moles of superacid precursor and 0.5 mole of Ph-[DYE-H]$^+$. After infra-red analysis to determine the amount of Ph-[DYE-H]$^+$, the infra-red irradiation may be adjusted so that, in exposed areas, only a further 0.4 mole of superacid precursor is decomposed by the dye. Thus, after the infra-red irradiation, the medium will contain 0.9 mole of the protonated product in exposed areas and 0.5 mole of the protonated product in unexposed areas.

If no change were made in the ultra-violet irradiation step described above with reference to Table 1, the results would be disastrous, since generation of a further 0.75 mole of acid in the unexposed areas would cause the acid concentration to exceed the threshold level, and the secondary acid generator would decompose in both the exposed and unexposed areas. Accordingly, based upon the results of the infra-red analysis, the ultra-violet irradiation is adjusted so that only (say) 0.4 mole of acid are decomposed in the exposed and unexposed areas. Accordingly, after the ultra-violet irradiation, the exposed areas contain 1.3 moles of acid (0.3 mole above threshold level) in the exposed areas and 0.9 mole (still below threshold level) in the unexposed areas. The slight reduction in the amount of unbuffered superacid in the exposed areas (0.3 mole, versus 0.5 mole in Table 1) will not significantly affect the results of the heating step, and the overall result of the imaging process will be unchanged.

For similar reasons, the present process is also relatively insensitive to variations in infra-red radiation, such as those caused by variations in laser output, variations between individual lasers in a laser diode array used to form the imaging beam, timing errors in laser drivers, etc. For example, in the process shown in Table 1, the infra-red irradiation causes decomposition of 0.75 mole of superacid precursor. If the infra-red radiation delivered to the imaging medium varies by ±20%, some exposed areas will experience decomposition of 0.6 mole of superacid precursor, while others will experience decomposition of 0.9 mole. After ultra-violet irradiation, the concentration of unbuffered superacid in the exposed areas will vary from 0.15 to 0.6 moles. In practice, with appropriate control of the heating step, this range of variation in unbuffered superacid concentration will have minimal effects on the final image.

Any of the known superacid precursors, for example diazonium, phosphonium, sulfonium and iodonium compounds, may be used in this invention, but iodonium compounds are preferred. Especially preferred superacid precursors are diphenyliodonium salts, specifically (4-octyloxyphenyl)phenyliodonium hexafluorophosphate and hexafluoroantimonate and bis(n-dodecylphenyl)iodonium hexafluoroantimonate.

Any infra-red dye capable of sensitizing decomposition of the superacid precursor with the production of superacid may be used in the present process. Preferably, the infra-red dye is a squarylium dye, since squarylium dyes tend to have high infra-red extinction coefficients, have long singlet excited state lifetimes (which assists the electron transfer reactions upon which the present process depends), show little tendency to aggregate in polymeric films, and have low visible absorptions. Examples of infra-red dyes useful in the present process are:

a) dyes comprising an inner salt of a compound of the formula:

$$Q^1{=}Z{-}Q^2$$

wherein:

$Q^1$ is a 4-(benz[b]-4H-pyrylium)methylidene, 4-(benz[b]-4H-thiopyrylium)methylidene or 4-(benz[b]-4H-selenopyrylium)methylidene grouping;

Z is a 1,3-(2-hydroxy-4-oxo-2-cyclobutylidene) hydroxide or 1,3-(2-hydroxy-4,5-dioxo-2-cyclopentylidene) hydroxide ring; and $Q^2$ is a 4-(benz[b]-4H-pyran-4-ylidene)methyl, 4-(benz[b]- 4H-thiopyran-4-ylidene)methyl or 4-(benz[b]-4H-selenopyran-4-ylidene)methyl grouping;

wherein at least one of the groupings $Q^1$ and $Q^2$ carries at its 2-position a substituent in which a non-aromatic carbon atom is bonded directly to the benzpyrylium, benzthiopyrylium or benzselenopyrylium nucleus, subject to the proviso that if said 2-substituent contains an aromatic nucleus, this aromatic nucleus is not conjugated with the benzpyrylium, benzthiopyrylium or benzselenopyrylium nucleus to which it is attached (see U.S. application Ser. No. 08/126,427, filed Sep. 24, 1993 in the names of Stephen J. Telfer et al., and assigned to the same assignee as the present application, and the corresponding International Application No. PCT/US91/08695, Publication No. WO 92/09661);

b) squarylium compounds of the formula:

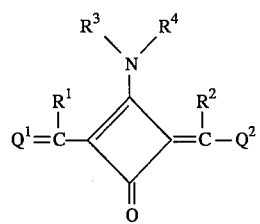

in which $Q^1$ and $Q^2$ are each a chromophoric group having an unsaturated system conjugated with the squarylium ring and such that in the compounds of formulae $Q^1CH_2R^1$ and $Q^2CH_2R^2$ the methylene hydrogens are active hydrogens, $R^1$ and $R^2$ are each independently a hydrogen atom or an aliphatic or cycloaliphatic group, and $R^3$ and $R^4$ are each independently a hydrogen atom, or an aliphatic, cycloaliphatic, aromatic or heterocyclic group, or one of $R^3$ and $R^4$ is a hydrogen atom and the other is an organosulfonyl group, or $R^3$ and $R^4$ together with the intervening nitrogen atom form a cycloaliphatic or aromatic ring (see U.S. Pat. No. 5,227,498 and the corresponding International Application No. PCT/US92/09992, Publication No. WO 93/09956); and c) squarylium compounds of the formula:

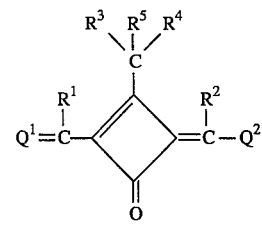

in which:

$Q^1$ and $Q^2$ are each a chromophoric group having an unsaturated system conjugated with the squarylium ring and such that in the compounds of formulae $Q^1CH_2R^1$ and $Q^2CH_2R^2$ the methylene hydrogens are active hydrogens;

$R^1$ and $R^2$ are each independently a hydrogen atom or an aliphatic or cycloaliphatic group; and $R^3$, $R^4$ and $R^5$ are each independently a hydrogen atom, or an aliphatic, cycloaliphatic, aromatic or heterocyclic group, or an electron-withdrawing group able to lower the electron density at the carbon atom to which it is attached, subject to the provisoes that:

two of $R^3$, $R^4$ and $R^5$ may form a divalent group of which a single atom is double bonded to the carbon atom to which the two groups are attached, or all three of $R^3$, $R^4$ and $R^5$ may form a trivalent group of which a single atom is triple bonded to the carbon atom to which the three groups are attached, or two of $R^3$, $R^4$ and $R^5$ may, together with the carbon atom to which they are attached, form a ring, or all three of $R^3$, $R^4$ and $R^5$ may, together with the carbon atom to which they are attached, form an unsaturated ring (see U.S. Pat. No. 5,227,499 and the corresponding International Application No. PCT/US92/09992, Publication No. WO 93/09956).

Any secondary acid generator which is capable of superacid-catalyzed breakdown to give a second acid may be used in the present process. One preferred group of secondary acid generators are 3,4-disubstituted-cyclobut-3-ene-1,2 diones (hereinafter for convenience referred to as "squaric acid derivatives") capable of generating squaric acid or an acidic derivative thereof, since squaric acid and its acidic derivatives are strong acids well suited to effecting color changes or other effects (for example, polymerization or depolymerization reactions) in acid-sensitive materials. Especially preferred squaric acid derivatives are those in which there is bonded to the squaric acid ring, via an oxygen atom, an alkyl or alkylene group, a partially hydrogenated aryl or arylene group, or an aralkyl group. The acid-catalyzed decomposition of these squaric acid derivatives causes replacement of the original alkoxy, alkyleneoxy, aryloxy, aryleneoxy or aralkoxy group of the derivative with a hydroxyl group, thereby producing squaric acid or an acidic squaric acid derivative having one hydroxyl group.

The exact mechanism by which squaric acid or an acidic derivative thereof is formed in the present process may vary depending upon the type of squaric acid derivative employed. In some cases, for example di-t-butyl squarate, one or both groups attached via oxygen atoms to the squaric acid ring may thermally decompose to yield an alkene or arene, thereby converting an alkoxy or aryloxy group to a hydroxyl group and forming the squaric acid or acidic derivative thereof. In other cases, for example 3-amino-4-(p-vinylbenzyloxy)cyclobut-3-ene-1,2-dione, there is no obvious mechanism for formation of a corresponding alkene or arene, and it appears that the mechanism of acid formation is migration of the vinylbenzyl carbocation or similar group to a different position within the molecule (probably to the amino group), and protonation of the remaining oxygen atom to form a hydroxyl group at the position from which the group migrates. In other cases, neither of these pathways is possible. However, in all cases the net effect is the replacement of the alkoxy, alkyleneoxy, aryloxy, aryleneoxy or aralkoxy group present in the original derivative with a hydroxyl group to form squaric acid or an acidic derivative thereof.

Those skilled in the art of organic chemistry will appreciate that the susceptibility to thermal decomposition of the squaric acid derivatives preferred for use in the present process is related to the stability of the cation which is produced from the ester grouping during the decomposition process. Although the stability of specific cations may be influenced by a variety of factors, including steric factors, which may be peculiar to a particular ester, in general it may be stated that the squaric acid esters preferred for use in the present process are:

(a) primary and secondary esters of squaric acid in which the α-carbon atom (i.e, the carbon atom bonded directly to the —O— atom of the squarate ring) bears a non-basic cation-stabilizing group. This cation-stabilizing group may be, for example, an $sp^2$ or sp hybridized carbon atom, or an oxygen atom;

(b) tertiary esters of squaric acid in which the α-carbon atom does not have an $sp^2$ or sp hybridized carbon atom directly bonded thereto; and (c) tertiary esters of squaric acid in which the α-carbon atom does have an $sp^2$ or sp hybridized carbon atom directly bonded thereto, provided that this $sp^2$ or sp hybridized carbon atom (or at least one of these $sp^2$ or sp hybridized carbon atoms, if more than one such atom is bonded directly to the α-carbon atom) is conjugated with an electron-withdrawing group. It will be apparent to skilled organic chemists that, provided one of the aforementioned types of ester groupings is present in the squaric acid derivative to produce one hydroxyl group after thermal decomposition, the group present in place of the other hydroxyl group of squaric acid is of little consequence, provided that this other group does not interfere with the thermal decomposition. Indeed, the wide variation possible in this other group has the advantage that this group can be varied to control other properties of the derivative, for example its compatibility with other components of the imaging medium, or its solubility in solvents used to form coating solutions used in the preparation of the imaging medium.

Examples of squaric acid derivatives useful in the present processes include:

(a) those of the formula:

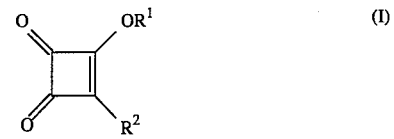

in which $R^1$ is an alkyl group, a partially hydrogenated aromatic group, or an aralkyl group, and $R^2$ is a hydrogen atom or an alkyl, cycloalkyl, aralkyl, aryl, amino, acylamino, alkylamino, dialkylamino, alkylthio, alkylseleno, dialkylphosphino, dialkylphosphoxy or trialkylsilyl group, subject to the proviso that either or both of the groups $R^1$ and $R^2$ may be attached to a polymer. Among the derivatives of Formula I, especially preferred groups are those in which (a) $R^1$ is an unsubstituted or phenyl substituted alkyl group containing a total of not more than about 20 carbon atoms, and $R^2$ is an alkyl group containing not more than about 20 carbon atoms, or a phenyl group (which may be substituted or unsubstituted); and (b) $R^1$ is a benzyl group and $R^2$ is an amino group.

(b) those of the formula:

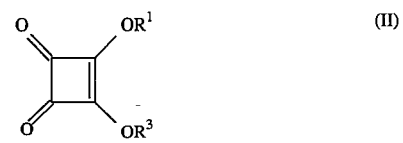

in which $R^1$ and $R^3$ independently are each an alkyl group, a partially hydrogenated aryl group or an aralkyl group, subject to the proviso that either or both of the groups $R^1$ and $R^3$ may be attached to a polymer. Among the derivatives of Formula II, an especially preferred group are those in which $R^1$ and $R^3$ are each independently an unsubstituted or phenyl substituted alkyl group containing a total of not more than about 20 carbon atoms. Specific preferred compounds of Formula II are those in which $R^1$ and $R^3$ are each a tertiary butyl group, a benzyl group, an α-methylbenzyl group or a cyclohexyl group, namely di-tertiary butyl squarate, dibenzyl squarate, bis(α-methylbenzyl) squarate and dicyclohexyl squarate.

(c) those of the formula:

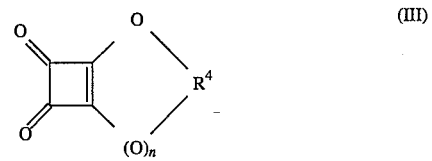

in which n is 0 or 1, and $R^4$ is an alkylene group or a partially hydrogenated arylene group. Among the derivatives of Formula III, an especially preferred group are those in which n is 1 and $R^4$ is an alkylene group containing not more than about 12 carbon atoms.

(d) those having at least one unit of the formula:

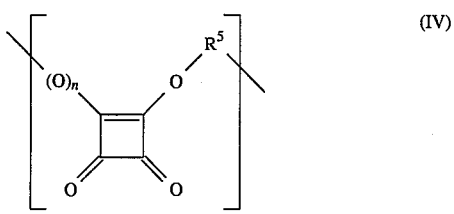

(IV)

in which n is 0 or 1, $R^5$ is an alkylene or partially hydrogenated arylene group. In addition to the fragmentable groups $R^5$, the compounds may also contain one or more units in which a non-fragmentable group is attached to a squarate ring, directly or via an oxygen atom.

The squaric acid derivatives of Formula IV include not only high polymers, but also dimers, trimers, tetramers, etc. including at least one of the specified units. The terminating groups on the derivatives of Formula IV may be any of groups $OR^1$ or $R^2$ discussed above with reference to Formula I. Thus, for example, Formula IV includes the squaric acid dimer derivative of the formula:

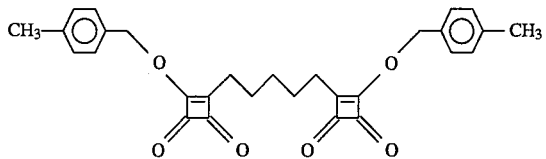

The squaric acid derivatives of Formulae I and II are usually monomeric. However, these derivatives of Formulae I and II can be incorporated into polymers by having at least one of the groups $R^1$, $R^2$ and $R^3$ attached to a polymer. Attachment of the squaric acid derivatives to a polymer in this manner may be advantageous in that it may avoid incompatibility and/or phase separation which might occur between a monomeric squaric acid derivative of Formula I or II and a polymeric binder needed in an imaging medium.

The attachment of the groups $R^1$, $R^2$ and $R^3$ to a polymer may be effected in various ways, which will be familiar to those skilled in the art of polymer synthesis. The squaric acid derivatives may be incorporated into the backbone of a polymer, for example in a polymer similar to the dimer of the formula given above. Alternatively, the squaric acid derivatives may be present as sidechains on a polymer; for example, one of the groups $R^1$, $R^2$ and $R^3$ could contain an amino group able to react with a polymer containing a carboxyl groups or derivatives thereof to form an amide linkage which would link the squaric acid derivative as a sidechain on to the polymer, or these groups may contain unsaturated linkages which enable the squaric acid derivatives to be polymerized, either alone or in admixture with other unsaturated monomers.

In the present process, it is generally undesirable to form substantial quantities of gas during the superacid-catalyzed decomposition of the squaric acid derivative (or other secondary acid generator) since such gas may distort the medium containing the squaric acid derivative or form vesicles therein, and such distortion or vesicle formation may interfere with proper image formation. Accordingly, if the decomposition of the squaric acid derivative yields an alkene, it is desirable that the groups $R^1$, $R^3$, $R^4$ and $R^5$ be chosen so that this alkene is a liquid at 20° C., and preferably higher, since some heating of the alkene will inevitably occur during the superacid-catalyzed decomposition. In some cases, however, the alkene liberated may be sufficiently soluble in the medium containing the squaric acid derivative that liberation of a highly volatile alkene will not result in distortion of, or vesicle formation in, the medium.

Another preferred group of secondary acid generators for use in the present process are oxalic acid derivatives which undergo superacid-catalyzed breakdown to give oxalic acid or an acidic derivative thereof, for example an oxalic acid hemiester. Although oxalic acid and its acidic derivatives are not quite such strong acids as squaric acid and its acidic derivatives, oxalic acid and its derivatives are sufficiently strong acids for most purposes for which secondary acids are required in the present process. Also, oxalic acid derivatives are, in general, less costly than squaric acid derivatives.

The types of oxalic acid derivatives preferred for use in the present process are rather more diverse in structure than the squaric acid derivatives, and the choice of oxalic acid derivative for any specific process may be governed more by the thermal breakdown properties of the derivative than its exact chemical structure; in general, for practical reasons such as the limited temperature range to which other components of the imaging medium may safely be exposed, it is preferred that the oxalic acid derivative be one which begins to decompose thermally at a temperature in the range of about 140° to about 180° C., as measured by differential scanning calorimetry in a nitrogen atmosphere at a 10° C./minute temperature ramp, in the absence of any catalyst. Since the presence of a superacid catalyst lowers the thermal decomposition temperature of oxalic acid derivatives by at least about 20° C. and potentially significantly more, derivatives which decompose uncatalyzed at about 140° to about 180° C., will, in the presence of superacid, decompose at temperatures as low as about 65° C., temperatures to which other components of the imaging medium can in general be exposed.

The factors affecting the ability of the oxalic acid derivatives to undergo superacid-catalyzed thermal decomposition are similar to those affecting the ability of the aforementioned squaric acid derivatives to undergo the same reaction, and thus the preferred ester groups are of the same types. Accordingly, preferred oxalic acid derivatives for use in the present process include:

(a) primary and secondary esters of oxalic acid in which the α-carbon atom (i.e, the carbon atom bonded directly to the —O— atom of the oxalate grouping) bears a non-basic cation-stabilizing group. This cation-stabilizing group may be, for example, an $sp^2$ or sp hybridized carbon atom, or an oxygen atom;

(b) tertiary esters of oxalic acid in which the α-carbon atom does not have an $sp^2$ or sp hybridized carbon atom directly bonded thereto; and (c) tertiary esters of oxalic acid in which the α-carbon atom does have an $sp^2$ or sp hybridized carbon atom directly bonded thereto, provided that this $sp^2$ or sp hybridized carbon atom (or at least one of these $sp^2$ or sp hybridized carbon atoms, if more than one such atom is bonded directly to the α-carbon atom) is conjugated with an electron-withdrawing group.

(d) an ester formed by condensation of two moles of an alcohol with the bis(hemioxalate) of a diol, provided that the ester contains at least one ester grouping of types (a), (b) or (c) above. One example of an ester of this type is that of the structure:

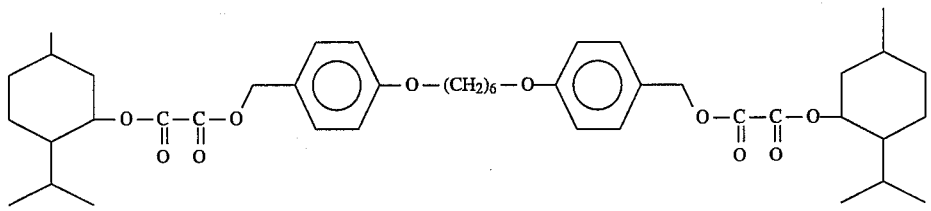

which can be regarded as formed from two moles of menthol (2-methylethyl-4-methylcyclohexanol) and one mole of the bis(hemioxalate) of 1,6-bis-(4-hydroxymethylphenoxy)hexane. Since the structure of the central residue of the diol in such esters can vary widely, the solubility and other properties of the esters can be "tuned" as required for compatibility with other components of the imaging medium, while the nature of the end groups, which undergo the acid-forming thermal decomposition, can be varied independently of the nature of the central residue.

(e) polymeric oxalates derived from polymerization of oxalate esters having an ethylenically unsaturated group, provided that the ester contains at least one ester grouping of types (a), (b) or (c) above. As with the squaric acid derivatives discussed above, use of a polymeric oxalate rather than a monomeric one may be advantageous in that it may avoid incompatibility and/or phase separation which might occur between a monomeric derivative and a polymeric binder needed in an imaging medium. Use of a polymeric derivative also tends to inhibit diffusion of the oxalate through the imaging medium during storage prior to imaging. Although polymeric oxalates can be formed in other ways, at present we prefer to form such oxalates by first forming an oxalate ester in which one of the ester groupings comprises an ethylenically unsaturated group, and then polymerizing this ester using a conventional free radical polymerization initiator, for example azobis(isobutyronitrile) (AIBN). The ethylenically unsaturated group is conveniently an acrylate or methacrylate group, while the other ester grouping in the monomeric oxalate can be any of the types discussed above.

(f) Condensation polymers of oxalates, provided that the ester contains at least one ester grouping of types (a), (b) or (c) above. This type of polymer also possesses the advantages discussed under (e) above.

As already mentioned, the present process may be used for various purposes, such as triggering of an acid-catalyzed chemical reaction (for example, polymerization or depolymerization reactions). When the present process is used for image formation, simultaneously with or subsequent to the heating step, the second acid is contacted with an acid-sensitive material which changes color in the presence of the second acid. (It will be appreciated that the "color change" involved in such an imaging process need not be a visible color change. If, for example, the present process is used to provide security markings intended to be machine-readable, the "color change" could be a change in absorption from one non-visible wavelength to another, such that it can be detected by the appropriate machine-reading device.)

The acid-sensitive material used in the process of the present invention may be any material which undergoes a color change in the presence of the second acid. Thus any conventional indicator dye may be used as the acid-sensitive material, as may the leuco dyes disclosed in the aforementioned U.S. Pat. Nos. 4,602,263; 4,720,449 and 4,826,976, which are also sensitive to acid.

The exposure of the medium to the actinic (typically infra-red) radiation of the first wavelength can be effected in any of the ways conventionally used for exposing media to the same type of radiation. In some cases, it may be convenient to employ a laser of the appropriate wavelength, since the use of a laser is a convenient way to record data as an image pattern in response to transmitted signals, such as digitized information.

Some imaging media of the present invention (for example those intended for use as photoresists and containing polymerizable monomers or oligomers or depolymerizable polymers) may comprise only a single layer containing all the components of the imaging medium. However, media containing a secondary acid generator and an acid-sensitive material desirably comprise two separate layers or phases, so that, prior to the heating, the acid-sensitive material is present in a layer or phase separate from the layer or phase containing the superacid precursor and the secondary acid generator, and following the generation of the second acid from the secondary acid generator, the two layers or phases are mixed, thereby effecting the color or other change in the acid-sensitive material.

In principle, the mixing of the acid-sensitive material with the superacid precursor, sensitizing dye and secondary acid generator should be effected after the generation of the second acid from the secondary acid generator. However, in practice if the superacid precursor, sensitizing dye and secondary acid generator are present in one layer of a two-layer imaging medium, and the acid-sensitive material in the other layer of the medium, these two layers being such that their diffusible components mix on heating, both the generation of the second acid and the mixing of the two layers may be effected in a single heating step, since the superacid-catalyzed decomposition of the secondary acid generator will typically be essentially complete before mixing of the two layers becomes significant.

When a two-layer structure is used, it is not necessary that the two layers be affixed to one another before imaging. The production of unbuffered superacid and second acid in exposed regions effected by the present processes are "permanent" chemical changes, and hence it is possible to delay contacting the exposed medium with an acid-sensitive material for a substantial time. (Obviously, excessive delay may reduce the quality of an image produced by allowing superacid or second acid to diffuse from exposed into unexposed areas of the medium.) Accordingly, the two layers of the imaging medium may be laminated together after the second irradiation. However, in general it is most convenient to form the two layers by coating one on the other, or laminating the two layers together before imaging, since in this way only a single sheet of material has to handled during the imaging process. Since it is important that the two layers not mix prematurely, if the two layers are to be coated successively on to a support, it is usually desirable to coat one layer from an aqueous medium and the other from a non-aqueous medium. Typically, the layer containing the superacid precursor is coated from an organic solution and the layer containing an acid-sensitive leuco dye or other material is coated from an aqueous dispersion.

As already mentioned above with reference to Table 1 and FIG. 1, prior to the heating step, the acid-sensitive material may be in admixture with an amount of a basic material insufficient to neutralize all the second acid liberated by the secondary acid generator during the heating, so that the second acid liberated by the secondary acid generator during the heating neutralizes all of the basic material and leaves excess second acid sufficient to effect the change in the acid-sensitive material. The provision of this basic material serves to "soak up" minor amounts of acid which may be generated in unexposed areas after exposure due, for example, to slow decomposition of the superacid precursor/sensitizing dye mixture during protracted storage. Since obviously the basic material cannot be allowed to contact the superacid present after the second irradiation but prior to the heating step, desirably the acid-sensitive material is present in a layer or phase separate from the layer or phase containing the superacid precursor and the secondary acid generator and, following the generation of the second acid, the two layers or phases are mixed, thereby effecting the change in the acid-sensitive material.

In addition to the two aforementioned layers or phases containing the superacid precursor, sensitizing dye, secondary acid generator and acid-sensitive material, the imaging media of the present invention may comprise a support and additional layers, for example, a subbing layer to improve adhesion to the support, acid-impermeable interlayers for separating multiple imaging layers from one another, an anti-abrasive topcoat layer, and other auxiliary layers.

The support employed may be transparent or opaque and may be any material that retains its dimensional stability at the temperature used for image formation. Suitable supports include paper, paper coated with a resin or pigment, such as, calcium carbonate or calcined clay, synthetic papers or plastic films, such as polyethylene, polypropylene, polycarbonate, cellulose acetate and polystyrene. The preferred material for the support is a polyester, desirably poly(ethylene terephthalate).

Usually the layer containing the superacid precursor, sensitizing dye, and secondary acid generator, and the layer containing the acid-sensitive material, will each also contain a binder; typically these layers are formed by combining the active materials and the binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking.

The binder used for the layer(s) in which superacid is to be generated must of course be non-basic, such that the superacid is not buffered by the binder. Examples of binders that may be used include styrene-acrylonitrile copolymers, polystyrene, poly($\alpha$-methylstyrene), copolymers of styrene and butadiene, poly(methyl methacrylate), copolymers of methyl and ethyl acrylate, poly(vinyl butyral), polycarbonate, poly(vinylidene chloride) and poly(vinyl chloride). It will be appreciated that the binder selected should not have any adverse effect on the superacid precursor, sensitizing dye, secondary acid generator or the acid-sensitive material incorporated therein. Also, the binder should be heat-stable at the temperatures encountered during the heating step and should be transparent so that it does not interfere with viewing of the image. The binder must of course transmit the actinic radiation used in the exposure steps.

The squaric acid derivatives preferably used as acid generators in the process of the present invention can be prepared by known methods, such as those described in U.S. Pat. No. 4,092,146 and Tetrahedron Letters (1977), 4437–38, and 23,361–4, and Chem. Ber. 121,569–71 (1988) and 113, 1–8 (1980). In general, the diesters of Formula II can be prepared by reacting disilver squarate with the appropriate alkyl halide(s), preferably the alkyl bromides. The ester groupings may be varied by routine transesterification reactions, or by reacting the diacid chloride of squaric acid with an appropriate alcohol or alkoxide.

Figure 2:
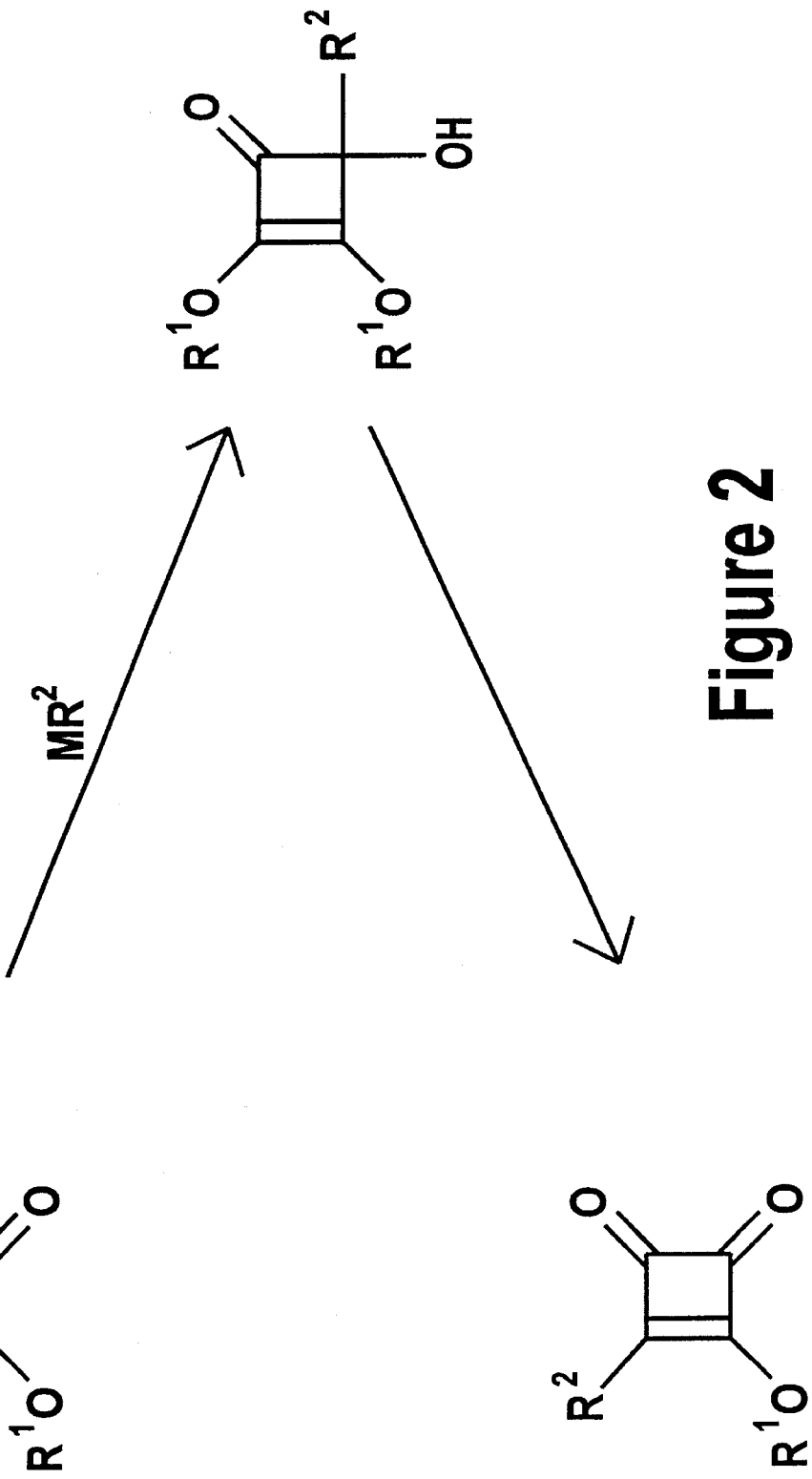
FIG. 2 shows a synthesis of a squaric acid derivative of Formula I below.
Figure 2:
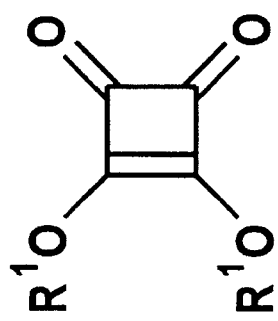
Figure 2:
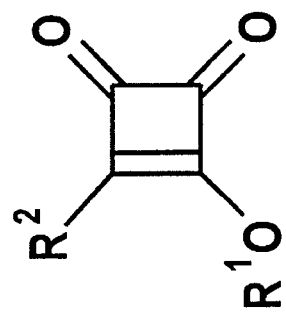

The derivatives of Formula I in which $R^2$ is an alkyl, cycloalkyl, aralkyl or aryl group can be prepared from derivatives of Formula II by the synthesis shown in FIG. 2. The diester of Formula II is first condensed with a compound containing a negatively charged species $R^2$; this compound is normally an organometallic compound, and preferably an organolithium compound. The reaction adds the -$R^2$ group to one of the oxo groups of the diester to produce the squaric acid derivative of Formula VI; to avoid disubstitution into both oxo groups, not more than the stoichiometric amount of the organometallic reagent should be used.

After being separated from unreacted starting material and other by-products, the squaric acid derivative VI is treated with an acid, for example hydrochloric acid, to convert it to the desired squaric acid derivative I. Although it is possible to simply add acid to the reaction mixture resulting from the treatment of the diester with the organometallic reagent, this course is not recommended, since the squaric acid derivative I produced may be contaminated with unreacted diester, and the diester and squaric acid derivative I are so similar that it is extremely difficult to separate them, even by chromatography.

It will be appreciated that the synthesis shown in FIG. 2 may be modified in various ways. If, for example, the nature of the group $R^1$ desired in the final compound of Formula I is such that it would react with the organometallic reagent, the reactions shown in FIG. 2 may be carried out with a diester in which the ester groupings do not contain the group $R^1$, and the final product of Formula I may be subjected to transesterification or other reactions to introduce the group $R^1$.

The derivatives of Formula I in which $R^2$ is an amino, alkylamino or dialkylamino group can be prepared by similar methods from squaric acid diesters. For example, as illustrated in the Examples below, reaction of bis(4-vinylbenzyl) squarate with methylamine gives 3-amino-4-(p-vinylbenzyloxy)cyclobut-3-ene-1,2-dione. Analogous methods for the synthesis of the other compounds of Formula I will readily be apparent to those skilled in the art of organic synthesis.

The forms of the squaric acid derivatives of Formulae I and II in which at least one of $R^1$, $R^2$ and $R^3$ is attached to a polymer may be prepared by reactions analogous to those used to prepare the monomeric derivatives of Formulae I and II, for example by treating a polymer containing appropriate alkoxide groups with the diacid chloride or a monoester monoacid chloride of squaric acid. Alternatively, these polymer-attached derivatives may be prepared by transesterification, for example by treating a polymer containing esterified hydroxyl groups with a monomeric squaric acid derivative of Formula I or II. Other methods for attachment of these derivatives to polymers, or inclusion of these derivatives into polymer backbones, have already been discussed above.

The derivatives of Formula III may be prepared by transesterification from derivatives of Formula II, or another squaric acid diester, and the appropriate diol.

The monomeric oxalic acid derivatives useful in the present process can be prepared by routine esterification techniques which will be familiar to those skilled in organic synthesis, and several Examples of such techniques are exemplified in detail below. The preparation of polymeric oxalic acid derivatives has already been discussed.

A preferred embodiment of the invention will now be described, though by way of illustration only, with reference to FIG. 3 of the accompanying drawings, which shows a schematic cross-section through an imaging medium (generally designated 10) of the invention as the image therein is being fixed by being passed between a pair of hot rollers 12.

The imaging medium 10 comprises a support 14 formed from a plastic film. Typically the support 14 will comprise a polyethylene terephthalate film 3 to 10 mils (76 to 254 mµ) in thickness, and its upper surface (in FIG. 3) may be treated with a sub-coat, such as are well-known to those skilled in the preparation of imaging media, to improve adhesion of the other layers to the support.

On the support 14 is disposed an acid-generating layer 16 comprising a superacid precursor, an infra-red sensitizing dye and a secondary acid generator, which undergoes a superacid-catalyzed thermal decomposition to form a second acid. On the opposed side of the acid-generating layer 16 from the support 14 is disposed a color-forming layer 18 comprising an acid-sensitive material, which changes color in the presence of an acid, and a small amount of a base. The acid-generating layer 16 and the imaging layer 18 both contain a binder having a glass transition temperature substantially above room temperature.

Finally, the imaging medium comprises an abrasion-resistant topcoat 20.

The imaging medium 10 may be formed by coating the layers 16, 18 and 20 on to the support 14. Alternatively, for example, the layers 16 and 18 may be coated on to the support 14, and the topcoat 20 laminated on to the resultant structure.

The imaging medium 10 is exposed by writing on selected areas of the medium with an infra-red laser; this exposure may be effected through the support 14, as indicated by the arrow 22 in the drawing (alternatively, exposure could be effected through the topcoat 20). Within the exposed regions of the acid-generating layer 16, the exposure to infra-red radiation causes breakdown of the superacid precursor with the formation of the corresponding superacid buffered by the sensitizing dye, as described above. After this infra-red exposure, the imaging medium 10 is passed beneath a mercury lamp and given a blanket ultraviolet exposure to produce unbuffered superacid in the infra-red exposed areas, and then passed between the heated rollers 12. The heat applied by the rollers 12 causes the superacid present in the exposed regions of the acid-generating layer 16 to cause catalytic breakdown of the secondary acid generator therein, thereby causing formation of a quantity of second acid substantially larger than the quantity of superacid originally generated by the ultra-violet radiation. The heat and pressure applied by the rollers 12 also raise the color-forming layer 18 and the acid-generating layer 16 above their glass transition temperatures, thereby causing the components dispersed in these two layers to become intermixed so that, in exposed regions, the second acid produced in the acid-generating layer 16 effects the color change of the acid-sensitive material, thereby forming an image.

Figure 3:
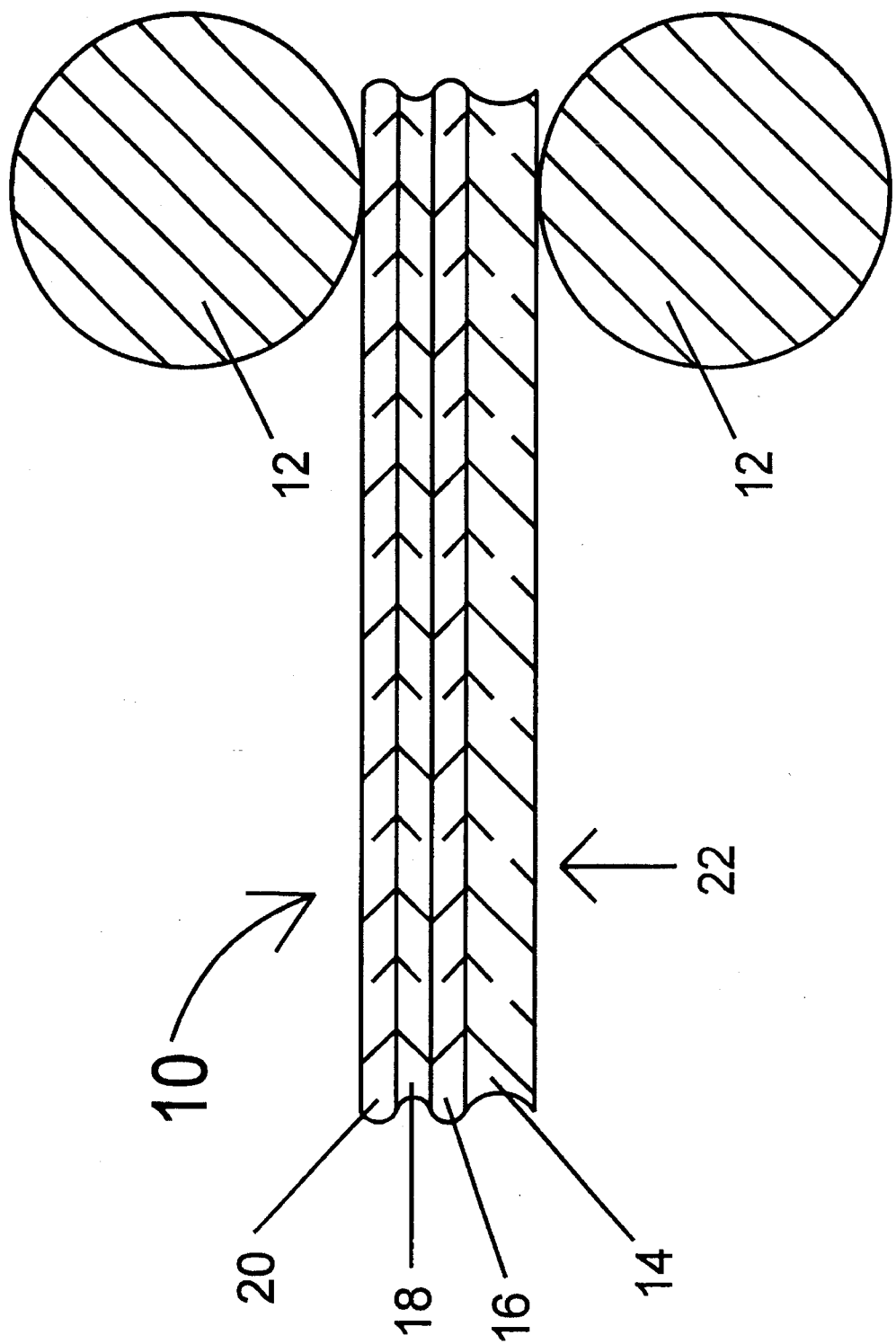
FIG. 3 is a schematic cross-section through an imaging medium of the present invention as it is being passed between a pair of hot rollers during the imaging process of the present invention.

The imaging medium 10 shown in FIG. 3 will produce monochrome images. As will readily be apparent to those skilled in the imaging art, this imaging medium 10 may readily be modified to produce full color images by including two or more additional pairs of color-forming layers 18 and acid-generating layers 16, with acid-impermeable interlayers provided between each adjacent pair of layers, the interlayers having a glass transition temperature sufficiently high that it is not exceeded during passage of the medium between the rollers 12, so that the interlayers prevent mixing of adjacent pairs of layers 16 and 18. Typically, a multicolor medium will comprise three pairs of color-forming layers 18 and acid-generating layers 16 arranged to produce yellow, cyan and magenta images, as in conventional multicolor imaging media. The acid-generating layers 16 in such a medium will contain infra-red sensitizing dyes absorbing at differing wavelengths so that the three color-forming layers can be imaged independently of one another using three infra-red lasers of differing wavelengths. It should be noted that only the infra-red sensitizing dyes need differ among the plurality of acid-generating layers; conveniently, all the acid-generating layers can make use of the same superacid precursor and secondary acid generator.

The following Examples are now given, though by way of illustration only, to show details of preferred reagents, conditions and techniques used in the process and imaging medium of the present invention.

EXAMPLES 1–11

Preparation of squaric acid derivative secondary acid generators 3,4-Bis(t-butoxy)cyclobut-3-ene-1,2-dione ("bis t-butyl squarate"; hereinafter referred to as "Compound A") used in certain Examples below was prepared as described in E. V. Dehmlow et al., Chem. Bet. 113, 1–8 (1980). 3,4-Bis(benzyloxy)cyclobut-3-ene-1,2-dione ("dibenzyl squarate"; hereinafter referred to as "Compound B") used in certain Examples below was prepared as described in N. Islam et al, Tetrahedron 43, 959–970 (1987). Silver squarate was prepared as described in S. Cohen et al., J. Am. Chem. Soc., 88, 5433 (1966).

Example 1

Preparation of bis(3-bromo-2,3-dimethylbut-2-yl)squarate

This Example illustrates the preparation of 3,4-bis(3-bromo-2,3-dimethylbut-2-oxy)-cyclobut-3-ene-1,2-dione ("bis(3-bromo-2,3-dimethylbut-2-yl) squarate"), the compound of Formula II in which $R^1$ and $R^3$ are each a 3-bromo-2,3-dimethylbut-2-yl group.

Silver squarate (1.0 g, 3.0 mmole) was added to a solution of 2,3-dibromo-2,3-dimethylbutane (1.0 g, 4.0 mmole) in dry ether (3 mL) at room temperature. The suspension became warm, and was cooled by a water bath at room temperature. After six hours' stirring, the precipitate remaining was removed by filtration, and washed with ether. The combined ether extracts were concentrated, and the crude product obtained therefrom was purified by flash chromatography on silica gel with 1:3 ether/hexanes as eluent to give the diester (140 mg, 11% yield) as a white powder which decomposed at 131°–132° C. The structure of the compound was confirmed by mass spectroscopy and by $^1H$ and $^{13}C$ NMR spectroscopy.

Example 2

Preparation of 3-t-butoxy-4-phenylcyclobut-3-ene-1,2-dione

This Example illustrates the preparation of 3-t-butoxy-4-phenyl-cyclobut-3-ene-1,2-dione, the compound of Formula I in which $R^1$ is a tertiary butyl group and $R^2$ is a phenyl group.

Phenyl magnesium bromide (4.6 mL of a 1.0M solution in THF, 4.6 mmole) was added dropwise over a period of 5 minutes to a solution of di-t-butyl squarate (1.0 g, 4.42 mmole) in dry ether (10 mL) at −78° C. under nitrogen. After 30 minutes, the reaction mixture was warmed to 0° C., and stirred at this temperature for an additional one hour. Water (10 mL) and ether (10 mL) were then added to the reaction mixture and the layers were separated. The aqueous layer was extracted twice with dichloromethane. The combined organic layers were dried over magnesium sulfate and concentrated, to give a yellow oil (1.43 g), which crystallized. The resultant material was dissolved in dichloromethane (25 mL) and concentrated hydrochloric acid (4 drops) was added, with stirring, to this solution at room temperature. After 30 minutes, a further four drops of concentrated hydrochloric acid were added. Dichloromethane (25 mL) was added, and the resultant solution was washed with a saturated solution of sodium bicarbonate and then with brine, dried over magnesium sulfate, and concentrated. The crude product thus obtained was purified by flash chromatography on silica gel with toluene as eluent. The chromatographed material was further purified by recrystallization from toluene/hexanes to give the desired monoester as yellow crystals (142 mg, 14% yield) which decomposed at 105°–110° C. The structure of this compound was confirmed by mass spectroscopy and by $^1$H and $^{13}$C NMR spectroscopy.

Example 3

Preparation of 3,4-bis(α-methylbenzyloxy)-cyclobut-3-ene-1,2-dione

This Example illustrates the preparation of 3,4-bis(α-methyl-benzyloxy)-cyclobut-3-ene- 1,2-dione ("bis(α-methylbenzyl) squarate"), the compound of Formula II in which $R^1$ and $R^3$ are each an α-methylbenzyl group.

1-Bromo-1-phenylethane (3.1 g, 16.8 mmole) was added dropwise to a suspension of silver squarate (2.5 g, 7.62 mmole) in dry ether (40 mL) at 0° C. After the addition was complete, the reaction mixture was allowed to warm to room temperature and was stirred for four hours in the dark. The solid remaining after this time (silver bromide) was removed by filtration and washed with more ether. The combined ether solutions were washed with a saturated solution of sodium bicarbonate and dried over sodium sulfate. Evaporation of the solvent was followed by purification by flash chromatography on silica gel with 0–60% ether/hexanes as eluant to give the desired diester (394 mg, 16% yield) as a colorless oil. The diester was obtained as a mixture of diastereoisomers which were not separable by this type of chromatography. The structure of the diester was confirmed by mass spectroscopy and by $^1$H and $^{13}$C NMR spectroscopy.

Example 4

Preparation of 3,4-bis(p-methylbenzyloxy)-cyclobut-3-ene-1,2-dione

This Example illustrates the preparation of 3,4-bis(p-methyl-benzyloxy)-cyclobut- 3-ene-1,2-dione ("bis(p-methylbenzyl)squarate"), the compound of Formula II in which $R^1$ and $R^3$ are each a p-methylbenzyl group.

Triethylamine (0.93 g, 9.2 mmole) was added to a stirred suspension of squaric acid (0.5 g, 4.38 mmole) in chloroform (10 mL) and the resultant solution was cooled with an ice/water bath. A solution of α-bromo-p-xylene (2.03 g, 11.0 mmole) in chloroform (10 mL) was then added dropwise over a period of 30 minutes. After this time, the cooling bath was removed and the solution was held at room temperature for 4.5 hours. The reaction mixture was then diluted with chloroform (20 mL), washed successively with a saturated aqueous solution of sodium bicarbonate (2×20 mL) and saturated brine (20 mL), dried over magnesium sulfate and concentrated under reduced pressure. The resultant oil was further purified by partition between ether (50 mL) and saturated aqueous sodium bicarbonate (20 mL) and separation of the organic layer. The organic layer was washed successively with a saturated aqueous solution of sodium bicarbonate (20 mL) and saturated brine (20 mL), dried over magnesium sulfate and concentrated under reduced pressure. The oil which resulted was crystallized from hot hexanes (20 mL) to give the desired compound (300 mg, 21.3% yield) as off-white crystals. The structure of this compound was confirmed by mass spectroscopy and by $^1$H and $^{13}$C NMR spectroscopy.

Example 5

Preparation of 3,4-bis(cyclohexyloxy)-cyclobut-3-ene-1,2-dione

This Example illustrates the preparation of 3,4-bis(cyclohexyloxy)-cyclobut- 3-ene-1,2-dione ("dicyclohexyl squarate"), the compound of Formula II in which $R^1$ and $R^3$ are each a cyclohexyl group.

Cyclohexyl bromide (9.95 g, 61 mmole) was added dropwise over a period of 20 minutes to a stirred suspension of silver squarate (4.0 g, 12.2 mmole) in ether (80 mL) in the dark with ice/water cooling. The ice bath was then removed and the reaction mixture was stirred overnight at room temperature, then filtered to remove silver bromide, and the residue was washed with ether (2×20 mL). The ether solutions were combined and washed successively with a saturated aqueous solution of sodium bicarbonate (50 mL) and saturated brine (50 mL), dried over magnesium sulfate and concentrated under reduced pressure to give the desired compound as a viscous oil which solidified upon storage in a refrigerator to give an off-white solid (0.55 g, 16% yield). The structure of this compound was confirmed by mass spectroscopy and by $^1$H and $^{13}$C NMR spectroscopy.

Example 6

Preparation of 3-amino-4-(t-butoxy)-cyclobut-3-ene-1,2-dione

This Example illustrates the preparation of 3-amino-4-(t-butoxy)-cyclobut- 3-ene-1,2-dione, the compound of Formula I in which $R^1$ is a tertiary butyl group and $R^2$ is an amino group.

A stream of ammonia gas was passed into a stirred solution of Compound A (0.7 g, 3.07 mmole) in methanol (40 mL) for 2 minutes. The solution was then allowed to stand at room temperature for 1 hour, during which time a small amount of insoluble material was precipitated. The sediment was removed by filtration, and the solvent was removed under reduced pressure to yield a yellow solid, which was washed with ether (2×50 mL) to remove starting material and butanol (0.16 g of impurities were collected, after solvent evaporation). The solid which remained was dissolved in dichloromethane (150 mL) and the solution was filtered. Removal of the solvent under reduced pressure yielded the desired compound as white crystals (0.25 g, 48% yield) which melted at 220°–225° C. The structure of this compound was confirmed by $^1$H NMR spectroscopy.

Example 7

Preparation of 4-hexyl-3-(p-vinyl-benzyloxy)cyclobut-3-ene-1,2-dione

This Example illustrates the preparation of 4-hexyl-3-(p-vinyl-benzyloxy)-cyclobut- 3-ene-1,2-dione, the compound of Formula I in which $R^2$ is a hexyl group and $R^1$ is an p-vinylbenzyl group.

Part A: Preparation of 2,3-dibutoxy-4-hexyl-4-hydroxy-cyclobut-2-en-1-one

Hexyl magnesium bromide (40 mL of a 2M solution in ether, 80.0 mmole) was added dropwise over a period of 45 minutes to a solution of di-n-butyl squarate in dry THF (150 mL) at −78° C. under nitrogen, and the reaction mixture was held at that temperature for 1 hour. The reaction mixture was then allowed to warm to room temperature are stirred for an additional 3 hours, after which time it was cooled using an ice/water bath, and quenched by the addition of water (25 mL) added dropwise over a period of 5 minutes. Saturated brine (300 mL) and ether (300 mL) were then added, the layers were separated, and the aqueous layer was extracted with additional ether (300 mL). The ether extracts were combined and dried over magnesium sulfate, and the solvents were removed to give a golden oil (15.64 g) containing the desired product; this oil was used without further purification in Part B below.

Part B: Preparation of 3-hexyl-4-hydroxy-cyclobut-3-ene-1,2-dione

6N Hydrochloric acid (150 mL) was added in one portion to a stirred solution of crude 2,3-dibutoxy-4-hexyl-4-hydroxycyclobut-2-en-1-one (15.1 g, prepared in Part A above) in THF (150 mL), and the resultant solution was stirred at room temperature for 3 hours. The reaction mixture was then concentrated under reduced pressure to give a yellow solid. To this solid was added water (100 mL), which was then removed under reduced pressure. Toluene (100 mL) was similarly added and removed under reduced pressure, and then dichloromethane (200 mL) was added to the residue and the resultant solution was filtered and concentrated to produce a yellow oil. Hexanes (200 mL) were added and the resultant solution was cooled to induce crystallization. After recrystallization from hexanes, the desired compound was isolated as tan crystals (4.28 g, 33% yield over Parts A and B). The structure of this compound was confirmed by mass spectroscopy and by $^1H$ and $^{13}C$ NMR spectroscopy.

Part C: Preparation of 4-hexyl-3-(p-vinylbenzyloxy)-cyclobut-3-ene-1,2-dione

Triethylamine (1.75 g, 17.3 mmoles),2,6-di-t-butyl-4-methylphenol (a radical inhibitor, 0.7 mg, 3.4 μmol) and 4-vinylbenzyl chloride (5.04 g, 33 mmole) were added, in that order, to a solution of 3-hexyl-4-hydroxy-cyclobut-3-en-1,2-one (3.0 g, 16.5 mmole, prepared in Part B above) in chloroform (90 mL), and the resultant solution was heated at reflux for 7 hours. The solution was then cooled and allowed to stand overnight at room temperature, after which it was heated at reflux for a further 7 hours, then cooled and allowed to stand overnight a second time. The reaction mixture was then concentrated under reduced pressure, the residue dissolved in dichloromethane (150 mL), and the resultant solution washed with water (2×75 mL), dried over magnesium sulfate and concentrated under reduced pressure to yield a yellow oil, which was purified by short-path distillation (to remove excess 4-vinylbenzyl chloride) at 72°–74° C. and 1.7 mm Hg pressure. The residue from the distillation was purified by flash chromatography on silica gel with dichloromethane as eluant to give the desired compound (1.23 g, 25% yield) as a golden oil. The structure of this compound was confirmed by mass spectroscopy and by $^1H$ and $^{13}C$ NMR spectroscopy.

Example 8

Preparation of 3-methylamino-4-(p-vinyl-benzyloxy)cyclobut-3-ene-1,2-dione

This Example illustrates the preparation of 3-methylamino-4-(p-vinyl-benzyloxy)-cyclobut- 3-ene-1,2-dione, the compound of Formula I in which $R^2$ is an amino group and $R^1$ is a p-vinylbenzyl group.

Part A: Preparation of bis(4-vinylbenzyl) squarate

4-Vinylbenzyl chloride (13 g, 85 mmole) was added to a suspension of silver squarate (5.5 g, 48 mmole) in dry ether (100 mL), and the resultant mixture was stirred in the dark for 3 days. The reaction mixture was then filtered and the solvent removed under reduced pressure. The residue was taken up in dichloromethane and filtered through a short column of silica gel, then concentrated under reduced pressure, to yield the desired compound in a crude form, which was used in Part B below without further purification.

Part B: Preparation of 3-methylamino-4-(p-vinylbenzyloxy)-cyclobut-3-ene-1,2-dione The crude product from Part A above was dissolved in ether (300 mL) and gaseous methylamine was bubbled through this ether solution for 1 minute. The resultant mixture was allowed to stand for 5 minutes, then the precipitate which had formed was removed by filtration, redissolved in chloroform and filtered through Celite (manufactured by Johns-Manville Corporation, Denver, Colo. 80217). The solvent was removed under reduced pressure to give the desired product (hereinafter called "Compound H") as a white solid, melting point 152° C. (3.5 g, 30% yield over Parts A and B). The structure of this compound was confirmed by $^1H$ NMR spectroscopy.

Example 9

Preparation of copolymer of Compound H with lauryl methacrylate

This Example illustrates the preparation of a 1:1 w/w copolymer of Compound H prepared in Example 8 above with lauryl methacrylate.

Compound H (1 g) and lauryl methacrylate (1 g) were dissolved in a mixture of 2-propanol (30 mL) and ethanol (20 mL), and the resultant solution was purged with nitrogen. Azoisobutyronitrile (0.01 g) was then added, and the solution was held at 65° C. overnight, during which time a precipitate (250 mg) formed. This precipitate was collected and shown by infra-red spectroscopy to contain squarate esters.

Example 10

Preparation of 4-[5-[1,2-dioxo-3-hydroxycyclobut-3-en-4-yl]pent-1-yl]-3-hydroxycyclobut-3-ene-1,2-dione Pentamethylene bis(magnesium bromide) (25 mL of a 0.5M solution in THF, 12.5 mmole) was added dropwise over a period of 15 minutes to a solution of dibutyl squarate (5.66 g, 25 mmole) in dry THF (50 mL) at −78° C. under a stream of nitrogen. The resulting suspension was stirred at −78° C. for 1 hour, then allowed to warm to room temperature and stirred for a further 2 hours. The homogeneous yellow solution which resulted was cooled to 0° C., and water (10 mL) was added dropwise over a period of 2 minutes. After standing for 5 minutes, the solution was diluted with THF (50 mL) and washed with saturated sodium chloride solution (150 mL). An emulsion was formed, which was separated by evaporative removal of THF and addition of dichloromethane (200 mL). The organic layer was separated and the aqueous layer was extracted with more dichloromethane (100 mL). The combined dichloromethane layers were dried over magnesium sulfate and concentrated under reduced pressure to yield a golden oil which was shown by thin layer chromatography, on silica gel with 1:1 ether/hexanes as eluent, to consist of five components.

This mixture was separated by flash chromatography on silica gel with 1:1 ether/hexanes, followed by pure ether, as eluents. Each of the five components was examined by $^1$H NMR spectroscopy. The third and fourth components (in order of elution from the column) were tentatively assigned as 4-[5-[1,2-dioxo-3-butoxy-cyclobut-3-en-4-yl]pent-1-yl]-3-butoxycyclobut-3-ene-1,2-dione (0.69 g) and 2,3-dibutoxy-[5-[1,2-dioxo-3-butoxycyclobut-3-en-4-yl]pent-1-yl]-4-hydroxycyclobut-2-en-1-one (2.14 g).

A portion of the isolated fourth component (2.01 g) was dissolved in THF (20 mL), and the resultant solution was treated with 6M hydrochloric acid (20 mL). The two-phase mixture became warm, and after 15 minutes stirring was observed to have become homogeneous. After a further two hours stirring, the solution was concentrated to dryness under reduced pressure. Water (20 mL) was added, and removed by evaporation, in order to drive off excess hydrogen chloride. The remaining water was removed by azeotropic distillation under reduced pressure with dichloromethane/acetone, to yield an off-white solid. This material was purified by recrystallization from THF/ether to yield the desired compound as a tan powder (542 mg, 18% yield over two steps). The structure of this compound was confirmed by $^1$H and $^{13}$C NMR spectroscopy.

Example 11

Preparation of 4-[5-[1,2-dioxo-3-[4-methyl-benzyloxy]cyclobut- 3-en-4-yl]pent-1-yl]-3-[4-methylbenzyloxy]cyclobut-3-ene-1,2-dione This Example illustrates the preparation of a dimeric squaric acid derivative in which two [4-methylbenzyloxy] cyclobut-3-ene-1,2-dione groups are linked via a pentamethylene chain.

Triethylamine (423 mg, 4.18 mmole) and p-methylbenzyl bromide (1.47 g, 7.96 mmole) were added sequentially to a suspension of 4-[5-[1,2-dioxo- 3-hydroxycyclobut-3-en-4-yl]pent-1-yl]-3-hydroxy-cyclobut-3-ene-1,2-dione (526 mg, 2.0 mmole, prepared in Example 10 above) in chloroform (15 mL) at room temperature, and the mixture was then heated at reflux for 9 hours. The solvent was removed under reduced pressure, and the resultant oil was purified by flash chromatography on silica gel with dichloromethane, followed by ether, as eluents. The product eluted with ether, and was obtained as a yellow oil (591 mg, 63% yield). The structure of this compound was confirmed by $^1$H and $^{13}$C NMR spectroscopy.

EXAMPLES 12–32

Preparation of oxalic acid derivative secondary acid generators

Example 12

Preparation of bis(2-methyl-2-hexyl)oxalate

To a solution of 2-methylhexan-2-ol (4.65 g, 40 mmole) and pyridine (4.74 g, 60 mmole) in tetrahydrofuran (15 mL) was added dropwise at 5°–10° C. over a period of 15 minutes a solution of oxalyl chloride (2.54 g, 20 mmole) in THF (6 mL). The resultant suspension was stirred at 20° C. overnight, then diluted with cold water (100 mL) and extracted with diethyl ether (65 mL). The organic layer was washed with cold dilute sulfuric acid, then with aqueous sodium bicarbonate, and finally with aqueous sodium chloride, then dried over sodium sulfate and evaporated to give the desired product as a pale yellow oil (3.25 g, 62% yield). An analytical sample was obtained by column chromatography on silica gel with 7% ethyl acetate in hexanes as eluent. The structure of this compound was confirmed by mass spectroscopy and by $^1$H and $^{13}$C NMR spectroscopy.

Example 13

Preparation of bis(α,α-dimethylbenzyl) oxalate

To a solution of α,α-dimethylbenzyl alcohol (5.44 g, 40 mmole) and pyridine (4.74 g) in THF (20 mL) was added dropwise at 5°–10° C. with stirring over a period of 25 minutes a solution of oxalyl chloride (2.54 g, 20 mmole) in THF (5 mL). The resultant suspension was stirred at 20° C. for 5 hrs, then poured into 140 mL of 0.5N sulfuric acid kept at 0° C. The oily product which separated was extracted with diethyl ether (60 mL) and the ether solution washed with saturated sodium bicarbonate (50 mL), and then with saturated aqueous sodium chloride (50 mL). The washed solution was dried over sodium sulfate and evaporated to give the desired product as a nearly colorless solid (5.745 g, 88% crude yield). A portion of this product was recrystallized from hexanes to provide colorless needles melting point 76.5°–79° C. The structure of this compound was confirmed by mass spectroscopy and by $^1$H and $^{13}$C NMR spectroscopy.

Example 14

Preparation of bis(p-butoxybenzyl) oxalate

To a solution of p-butoxybenzyl alcohol (1.803 g, 10 mmole) and pyridine (1.185 g, 15 mmole) in dichloromethane (10 mL) was added dropwise over a period of 5 minutes a solution of oxalyl chloride (0.635 g, 5 mmole) in methylene chloride (7 mL) at a temperature of 5°–20° C. The resultant suspension was stirred at 20° C. overnight, diluted to 50 mL with methylene chloride, then washed successively with water, dilute sulfuric acid, and aqueous sodium bicarbonate, and finally with brine. The washed suspension was then dried over sodium sulfate and evaporated to give the desired product (1.97 g, 76% yield) as colorless plates, melting point 113.5°–114.5° C. The structure of this compound was confirmed by mass spectroscopy and by $^1$H and $^{13}$C NMR spectroscopy.

Example 15

Preparation of bis(α-methylbenzyl)oxalate

To a solution of d,l-α-methylbenzyl alcohol (2.443 g, 20 mmole) and pyridine (2.37 g, 30 mmole) in dichloromethane (20 mL) was added at 5° C. a solution of oxalyl chloride (1.27 g, 10 mmole) in dichloromethane (8 mL). The resultant suspension was stirred at 0° C. for 20 minutes, and then at 20° C. overnight. The suspension was then poured into ice-water and acidified with 1N sulfuric acid (20 mL). The organic layer was washed with dilute sodium bicarbonate solution, then with brine, dried over sodium sulfate and evaporated to give the desired product as a pale yellow oil (2.661 g, 89% yield). The structure of this compound was confirmed by mass spectroscopy and by $^1$H and $^{13}$C NMR spectroscopy.

Example 16

Preparation of bis(p-methoxy-α-methylbenzyl)oxalate

To a solution of d,l-p-methoxy-α-phenethyl alcohol (3.57 g, 23.4 mmole) in dichloromethane (35 mL) containing 2.78 g (35.8 mmole) of pyridine was added over a period of 20 minutes at 0° C. a solution of oxalyl chloride (1.49 g, 11.8 mmole) in dichloromethane (6 mL). The resultant mixture was stirred at 20° C. for 14 hours, then poured into cold dilute sulfuric acid. The organic layer was washed with cold water, then with dilute sodium bicarbonate, dried over sodium sulfate and evaporated to give the desired product as a colorless oil (4.11 g, 97% yield). A 1.2 gram sample of this oil was crystallized from methanol to provide 0.51 g of product as fine matted plates of a mixture of diastereomers melting at 63°–82° C. The structure of this compound was confirmed by mass spectroscopy and by $^1$H and $^{13}$C NMR spectroscopy.

Example 17

Preparation of bis(p-methylbenzyl) oxalate

To a solution of p-methylbenzyl alcohol (3.33 g, 27 mmole) in pyridine (7 mL) was added at 0° C. over a period of five minutes oxalyl chloride (0.87 mL, 1.27 g, 10 mmole). The resultant reaction mixture was stirred at 0°–10° C. for one hour, then poured into cold dilute sulfuric acid to give a colorless precipitate, which was collected by filtration and washed with cold water to give colorless plates. These plates were recrystallized from methanol and then from hexanes as matted needles. The needles were recrystallized from methanol (30 mL) to provide the desired product (0.96 g, 32% yield), melting point 100°–100.5° C. A second crop of the product (1.20 g, 40% yield) was obtained by concentration of the mother liquors. The structure of the product was confirmed by mass spectroscopy and by $^1$H and $^{13}$C NMR spectroscopy.

Example 18

Preparation of ethyl p-methoxybenzyl oxalate

To a solution of p-methoxybenzyl alcohol (4.49 g, 14.4 mmole) and pyridine (1.92 g, 24.3 mmole) in dichloromethane (10 mL) was added at 5°–20° C. a solution of ethyl oxalyl chloride (2.216 g, 16.2 mmole) over a period of 4 minutes. The resultant reaction mixture was stirred at 0° C. for 20 minutes and then at 20° C. overnight. The reaction mixture was then poured into ice-water and acidified with 1N sulfuric acid (20 mL). The organic layer was washed with dilute sodium bicarbonate, then with brine, dried over sodium sulfate and evaporated to give the desired product (3.367 g) as a colorless solid. Recrystallization from hexanes provided colorless fine irregular prisms, melting point 44°–45° C. The structure of this compound was confirmed by mass spectroscopy and by $^1$H and $^{13}$C NMR spectroscopy.

Example 19

Preparation of 2,2-dimethyl-1-[4-methoxybenzyloxalyloxy] prop-3-yl [4-methoxybenzyl]oxalate A solution of 2,2-dimethylpropane-1,3-diol (24.6 g, 0.236 mole) in dichloromethane (200 mL) was added in a slow stream to a solution of oxalyl chloride (60.0 g, 0.472 mole) in dichloromethane (400 mL) which had been pre-cooled to 0° C. using an ice bath, the addition being made at such a rate that the temperature of the solution did not exceed 10° C. The resultant clear solution was allowed to warm to room temperature over a period of 30 minutes, and stirred for an additional 30 minutes, then cooled to 0° C. and pyridine (75 g, 0.948 mole) was added, again at such a rate as to maintain the temperature of the reaction mixture below 10° C. To the resultant yellow suspension was added a solution of 4-methoxybenzyl alcohol (65.35 g, 0.473 mole) in dichloromethane (100 mL), again keeping the temperature of the reaction mixture to 10° C. or below. After the addition had been completed, a cream-colored precipitate was observed. The reaction mixture was allowed to warm to room temperature and stirred overnight.

The mixture was then filtered, and the hygroscopic precipitate of pyridinium chloride was washed with dichloromethane (2×25 mL). The combined organic extracts were washed with: a) water (500 mL) containing concentrated hydrochloric acid (25 mL); b) water (700 mL) containing sodium hydrogen carbonate (50 g) and c) saturated brine (250 mL). The organic layer was then dried over anhydrous sodium sulfate and concentrated under reduced pressure. The residue was stirred with ether (500 mL) for 10 minutes, then filtered. The precipitate (which was the unwanted by-product, 4-methoxybenzyl oxalate) was washed with more ether (2×25 mL), and the combined ether solutions were concentrated under reduced pressure to give a waxy solid (93.88 g), which resisted attempts at recrystallization. Purification was, however, effected by trituration with cold methanol (500 mL) to afford the desired compound (68.5 g, 59% yield) as a white powder, melting point 38°–40° C. The structure of this compound was confirmed by mass spectroscopy and by $^1$H and $^{13}$C NMR spectroscopy.

Example 20

Preparation of 2,2-dimethyl-1-[4-benzyloxy[benzyloxalyloxy]]prop-3-yl [4-methoxybenzyl]oxalate Example 19 was repeated except that the 4-methoxybenzyl alcohol was replaced by 4-benzyloxybenzyl alcohol, to give the above compound in 73% yield. This compound had a melting point of 73°–74 C., and its structure was confirmed by mass spectroscopy and by $^1$H and $^{13}$C NMR spectroscopy.

Example 21

Preparation of 1-[4-methoxybenzyloxalyloxy]]hex-6-yl [4-methoxybenzyl]oxalate

Example 19 was repeated except that the 2,2-dimethylpropane-1,3-diol was replaced by hexane-1,6-diol, to give the above compound in 49% yield. This compound had a melting point of 114°–115° C., and its structure was confirmed by mass spectroscopy and by $^1$H and $^{13}$C NMR spectroscopy.

Example 22

Preparation of cyclohexyl [4-[6-[4-[[cyclohexyloxalyloxy] methyl] phenoxy]hex-6-yloxy]benzyl]oxalate Part A: Preparation of 4-[1-[4-hydroxymethylphenoxy] hex- 6-yloxy]benzyl alcohol 4-Hydroxybenzyl alcohol (24.82 g, 0.2 mole) was added to a stirred suspension of finely ground potassium carbonate (42.0 g, 0.4 mole) in dry dimethylformamide (250 mL). The resultant mixture was stirred at 60° C. under dry nitrogen for 10 minutes, then 1,6-dibromohexane (24.4 g, 0.1 mole) was added. The reaction mixture was maintained at 60° C. for 5 hours, then allowed to cool to room temperature and stirred for 17 hours. The reaction mixture was then poured slowly into ice/water (800 mL). A tan precipitate formed, which was collected by filtration, washed with water, and dried in air to give a sticky solid. This material was triturated with 2-propanol (100 mL) and then with cold water (200 mL), to give the desired product as a powder (13.8 g, 42% yield) which was collected by (slow and difficult) filtration. The compound melted at 96°–110° C., and its structure was confirmed by mass spectroscopy and by $^1$H and $^{13}$C NMR spectroscopy.

Part B: Preparation of cyclohexyl [4-[6-[4-[[cyclohexyloxalyloxy] methyl]phenoxy]hex-6-yloxy]benzyl]oxalate A solution of cyclohexanol (2.0 g, 0.02 mole) in dichloromethane (50 mL) was added over a period of 15 minutes to a solution of oxalyl chloride (2.54 g, 0.02 mole) in dichloromethane (50 mL) cooled on an ice bath. The resultant solution was allowed to warm to room temperature over a period of 20 minutes, then stirred for a further 30 minutes, then again cooled, using an ice bath, and pyridine (3.16 g, 0.04 mole) was added over a two minute period. After 5 minutes standing, solid 4-[1-[4-hydroxymethylphenoxy] hex-6-yloxy]benzyl alcohol (prepared in Part A above, 3.30 g, 0.01 mole) was added in portions over a period of 15 minutes. The slightly turbid solution which formed was allowed to warm to room temperature and stirred for about 30 hours under nitrogen. This solution was then washed with: a) water (100 mL) containing concentrated hydrochloric acid (10 mL); b) saturated aqueous sodium hydrogen carbonate (100 mL) and c) saturated brine (50 mL). The organic layer was then dried over anhydrous sodium sulfate. Charcoal and Celite were added, and the solution was then filtered through Celite. After concentration of the filtrate under reduced pressure, the residue was purified by flash chromatography on silica gel with dichloromethane as eluent, giving the desired compound as a pale yellow oil (0.65 g, 10% yield). The structure of this compound was confirmed by mass spectroscopy and by $^1$H and $^{13}$C NMR spectroscopy.

Example 23

Preparation of adamantyl [4-[6-[4-[[adamantyloxalyloxy] methyl] phenoxy]hex-6-yloxy]benzyl]oxalate Example 22, Part B was repeated except that the cyclohexanol was replaced by an equimolar amount of adamantanol. The above compound was produced as a pale yellow oil in 22% yield, and its structure was confirmed by mass spectroscopy and by $^1$H and $^{13}$C NMR spectroscopy.

Example 24

Preparation of Menthyl [4-[6-[4-[[menthyloxalyloxy]methyl]phenoxy] hex-6-yloxy]benzyl]oxalate Example 22, Part B was repeated except that the cyclohexanol was replaced by an equimolar amount of d,l-menthol. The above compound was produced as a pale yellow oil in 22% yield, and its structure was confirmed by mass spectroscopy and by $^1$H and $^{13}$C NMR spectroscopy.

Example 25

Preparation of 2-methacryloxyethyl p-methoxybenzyl oxalate

Part A: Preparation of 2-methacryloxyethyl oxalyl chloride

Oxalyl chloride (50 g) and dichloromethane (50 g) were mixed and cooled, with stirring, in an ice bath to 7°–10° C. To the resultant mixture was added 2-hydroxyethyl methacrylate (40 g) over a period of 30 minutes. The resultant mixture was stirred overnight at room temperature under a slow stream of nitrogen, then concentrated on a rotary evaporator for one hour to yield the desired product as a colorless oil (65 g), which was sufficiently pure to be used in Part B below without further purification.

Part B: Preparation of 2-methacryloxyethyl p-methoxybenzyl oxalate p-Methoxybenzyl alcohol (14 g, approximately 0.1 mole) and pyridine (11 g, 0.13 mole) were dissolved in dichloromethane (100 mL) and cooled in an ice bath to 2°–4° C. Separately, the product of Part A above (25 g, 0.11 mole) was dissolved in dichloromethane (25 mL) and cooled in an ice bath. The second solution was added gradually to the first over a period of 25 minutes while keeping the temperature at 2°–4° C. The resultant reaction mixture was allowed to stand at room temperature overnight, then filtered then filtered through a plug of silica to remove a low $R_f$ impurity detectable by thin layer chromatography (TLC). The dichloromethane was then removed by evaporation to yield the desired product as a colorless oil (29 g, 91% yield over two stages). TLC with dichloromethane as eluent gave a single spot, $R_f$ 0.45. The structure of the product was confirmed by $^1$H NMR spectroscopy in deuterochloroform, the spectrum being as follows: δ=7.28 (doublet, 2H); 6.83 (doublet, 2H); 6.05 (singlet, 1H); 5.50 (singlet, 1H); 5.17 (singlet, 2H); 4.43 (triplet, 2H); 4.37 (triplet, 2H); 3.72 (singlet, 3H); and 1.86 (singlet, 3H) ppm.

Example 26

Preparation of poly(2-methacryloxyethyl p-methoxybenzyl oxalate)

The product of Example 25 above (29 g) was dissolved in toluene (200 mL) and azobis(isobutyronitrile) (AIBN; 0.3 g) was added. The resultant mixture was heated at 65° C. under nitrogen for 16 hours, additional AIBN (0.2 g) was added, and the mixture was heated under nitrogen for a further 24 hours. A polymeric product precipitated as a swollen gel, from which the supernatant liquor was decanted. The gel was washed repeatedly with diethyl ether, whereupon it deswelled and hardened. The washed polymer was dried in vacuo at 40° C. to yield the desired polymer (26 g, approximately 90% yield) as a non-sticky white solid, glass transition temperature ($T_g$) 65° C., decomposing at 210° C. in the absence of any catalyst.

Example 27

Preparation of 4-methacryloxybutyl p-methoxybenzyl oxalate

Example 25 above was repeated, except that 4-hydroxybutyl methacrylate was substituted for 2-hydroxyethyl methacrylate. The product was obtained as a colorless oil (yield 85%) and its structure was confirmed by $^1$H NMR spectroscopy in deuterochloroform, the spectrum being as follows: δ=7.28 (doublet, 2H); 6.83 (doublet, 2H); 6.05 (singlet, 1H); 5.50 (singlet, 1H); 5.17 (singlet, 2H); 4.23 (triplet, 2H); 4.13 (triplet, 2H); 3.72 (singlet, 3H); 1.86 (singlet, 3H) and 1.72 (multiplet, 4H) ppm.

Example 28

Preparation of poly(4-methacryloxybutyl p-methoxybenzyl oxalate)

The product of Example 27 above (5 g) was dissolved in toluene (25 mL) and AIBN (0.025 g) was added. The resultant mixture was heated at 65° C. under nitrogen for 16 hours, and then poured into hexane, whereupon the desired polymeric product precipitated, $T_g$ approximately 50° C., decomposing above 200° C. in the absence of any catalyst.

Example 29

Preparation of 4-benzyloxybenzyl 2-methacryloxyethyl oxalate

Example 25, Part B above was repeated, except that 4-benzyloxybenzyl alcohol was substituted for p-methoxybenzyl alcohol. The product was obtained as a white solid, melting point 4°–42° C. (yield 85%) and its structure was confirmed by $^1$H NMR spectroscopy in deuterochloroform, the spectrum being as follows: $\delta$=7.4 (multiplet, 5H); 7.28 (doublet, 2H); 6.85 (doublet, 2H); 6.07 (singlet, 1H); 5.52 (singlet, 1H); 5.23 (singlet, 2H); 5.02 (singlet, 2H); 4.45 (triplet, 2H); 4.35 (triplet, 2H); and 1.88 (singlet, 3H) ppm.

This monomer was converted to its homopolymer in the same manner as described in Example 28 above.

Example 30

Preparation of ethyl 4-(4-vinylbenzyloxy)benzyl oxalate

Part A: Preparation of 4-(4-vinylbenzyloxy)benzyl alcohol

A solution of potassium hydroxide pellets (3.2 g, 0.05 mole) in 50 mL of ethanol was prepared and stirred in a flask under nitrogen. Separately, p-hydroxybenzyl alcohol (6.2 g, 0.05 mole) and p-vinylbenzyl chloride (7.6 g, 0.05 mole) were dissolved in 50 ml of ethanol. The second solution was added to the first with stirring under nitrogen, and the resultant mixture was heated to 65° C. overnight. The reaction mixture was then cooled to room temperature and filtered, and solvent was removed from the filtrate on a rotary evaporator to give a tan solid. This solid was extracted with warm water, filtered off and dried, extracted with petroleum ether, filtered off and finally recrystallized from toluene/hexane to yield the desired product as a colorless solid (6 g, approximately 50% yield), melting point 110°–112° C. Its structure was confirmed by $^1$H NMR spectroscopy in deuterochloroform, the spectrum being as follows: $\delta$=7.38 (two doublets, J=10 Hz, 4H); 7.23 (doublet, J=10 Hz, 2H); 6.85 (doublet, J=10 Hz, 2H); 6.67 (two doublets, J=10 and 18 Hz, 1H); 5.72 (doublet, J=18 Hz, 1H); 5.21 (doublet, J=10 Hz, 1H); 5.0 (singlet, 2H); 4.57 (singlet, 2H); and 1.6 (singlet, 1H) ppm.

Part B: Preparation of ethyl 4-(4-vinylbenzyloxy)benzyl oxalate

The product of Part A above (4.8 g, 0.02 mole) and pyridine (2.0 g, 0.025 mole) were dissolved in dichloromethane (50 mL) and cooled to 10°–12° C. To this solution was added over a period of 10 minutes a solution of ethyloxalyl chloride (3 g, 0.022 mole) in dichloromethane (5 mL). TLC of the reaction mixture after the addition had been completed indicated that only a trace of the alcohol starting material remained. The reaction mixture was then filtered through a plug of silica to remove the pyridine salt produced, and the filtrate was concentrated to produce the desired produce as white crystals (approximately 90% yield) melting point 93° C. Its structure was confirmed by $^1$H NMR spectroscopy in deuterochloroform, the spectrum being as follows: $\delta$=7.35 (two doublets, J=10 Hz, 4H); 7.25 (doublet, J=10 Hz, 2H); 6.85 (doublet, J=10 Hz, 2H); 6.67 (two doublets, J=10 and 18 Hz, 1H); 5.72 (doublet, J=18 Hz, 1H); 5.21 (doublet, J=10 Hz, 1H); 5.18 (singlet, 2H); 5.0 (singlet, 2H); 4.27 (quadruplet, J=8 Hz, 2H); and 1.28 (triplet, J=8 Hz, 3H) ppm

Example 31

Preparation of poly(ethyl 4-(4-vinylbenzyloxy)benzyl oxalate)

The product of Example 30 above (approximately 2 g) was dissolved in toluene (25 mL) and AIBN (0.01 g) was added. The resultant mixture was heated at 65° C. under nitrogen for 16 hours. Proton NMR analysis indicated only about 50% polymerization, so additional AIBN (0.015 g) was added, and the mixture was heated at 65° C. under nitrogen for a further 16 hours. The resultant slightly viscous solution was poured into a 1:1 v/v mixture of diethyl ether and petroleum ether to precipitate the polymer, which was then treated with petroleum ether for deswelling. After drying, the desired polymer (approximately 0.7 g) was obtained as an off-white powder. Proton NMR analysis revealed no trace of remaining monomer.

Example 32

Preparation of 4-(4-vinylbenzyloxy)benzyl oxalate

3-Phenylpropyloxalyl chloride was prepared by reacting oxalyl chloride with 3-phenylpropanol in dichloromethane at 10° C. Example 30, Part B was then repeated using the 3-phenylpropyloxalyl chloride in place of ethyloxalyl chloride, to produce the product as fine white crystals, melting point 80° C. (81% yield). Its structure was confirmed by $^1$H NMR spectroscopy in deuterochloroform, the spectrum being as follows: $\delta$=7.1–7.4 (multiplet, 9H); 7.27 (doublet, 2H); 6.87 (doublet, 2H); 6.67 (two doublets, 1H); 5.72 (doublet, 1H); 5.22 (doublet, 1H); 5.20 (singlet, 2H); 5.03 (singlet, 2H); 4.21 (triplet, 2H); 2.65 (triplet, 2H); and 2.0 (two triplets, 2H) ppm.

Polymerization of this monomer in the same manner as in Example 31 above gave the corresponding polymer in a yield of 75%. This polymer as found to give good results as a secondary acid generator.

Imaging and other processes of the invention

EXAMPLE 33

Polymerization process of the invention using squaric acid derivative

This Example illustrates a process of the present invention in which the superacid generated after infra-red and ultra-violet irradiation is used to cause polymerization of a difunctional epoxy monomer.

A coating fluid was prepared by dissolving a silicone diepoxy monomer of the formula:

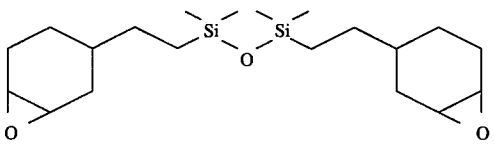

(supplied by General Electric Company, 40 mg), t-butylanthracene (5 mg; a precursor sensitizer), an infra-red dye of the formula:

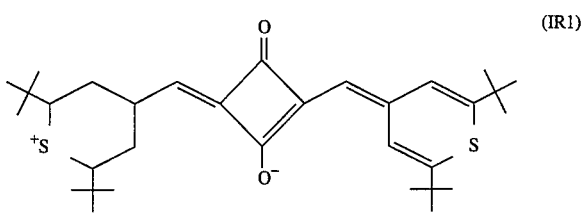

(IR1)

(see U.S. Pat. No. 4,508,811, 0.3 mg), (4-octyloxyphenyl)phenyliodonium hexafluoroantimonate (8 mg, prepared as per U.S. Pat. No. 4,992,571), and poly(vinyl chloride)

(supplied by Aldrich Chemical Company, Milwaukee, Wis., 30 mg) in methyl ethyl ketone (MEK, 0.6 mL). This solution was coated on to a poly(ethylene terephthalate) base 4 mil(101 µm) in thickness (ICI Type 3295, supplied by ICI Americas, Inc., Wilmington, Del.) using a number 18 coating rod.

The coated side of the resultant coating was exposed to infra-red radiation from a GaAlAs semiconductor diode laser emitting at 822 nm, which delivered 125 mW to the medium. The laser output was focussed to a spot approximately 33×3 µm. The medium was wrapped around a drum whose axis was perpendicular to the incident laser beam. Rotation of the drum about its axis and simultaneous translation in the direction of the axis caused the laser spot to write a helical pattern on the medium. The pitch of the helix was 33 µm, chosen so that none of the medium was left unexposed between adjacent turns. In this arrangement, the exposure received by the medium was inversely proportional to the speed of rotation of the drum (here measured as a linear speed at the medium surface). Separate bands of the medium were exposed at 2.0, 2.5, 3.0, 3.5 and 4.0 m/s.

Following this infra-red exposure, the entire coating was exposed for 70 seconds to ultra-violet radiation from a Universal UV unit (nominally emitting at 375 nm) supplied by Gelman Instrument Company. The coating was next heated on a hotplate at 100° C. for 20 seconds, after which the coating was developed by washing sequentially with methyl ethyl ketone and dichloromethane. Residual material was finally removed by sonication in a bath of methyl ethyl ketone for three minutes. In all areas which had received the infra-red exposure, insoluble polymeric material remained adhering to the polyester base and was not removed by the solvent treatment or sonication, whereas in all other areas of the film, including those areas which had received ultra-violet but not infra-red irradiation, no polymeric material was left adhering to the base after these treatments.

EXAMPLE 34

Imaging process of the invention using a squaric acid derivative as acid generator This Example illustrates an imaging process of the invention in which the imaging medium contains a secondary acid generator which amplifies the unbuffered superacid present in infra-red exposed areas following the infra-red and ultra-violet irradiations.

Two coating fluids were prepared as follows:

Fluid A: t-Butyl-anthracene (7 mg), the infra-red dye IR1 described in Example 33 above (0.3 mg), (4-octyloxyphenyl)phenyliodonium hexafluoroantimonate (5 mg), 3,4-bis(4-methylbenzyloxy)cyclobut-3-en-1,2-dione (20 mg) and a copolymer of vinylidene chloride and acrylonitrile (Saran Resin F120, available from Aldrich Chemical Company, Milwaukee, Wis., 30 mg) were dissolved in methyl ethyl ketone (0.6 mL).

Fluid B: A leuco dye of the formula:

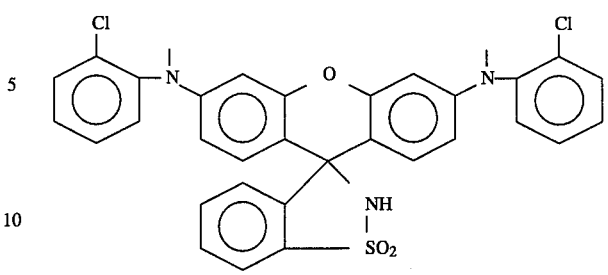

(15 mg; this leuco dye may prepared by the procedure described in U.S. Pat. No. 4,345,017) and a hindered amine base (HALS-62, available from Fairmount Chemical Company, Inc., 117 Blanchard Street, Newark N.J. 07105, 7 mg) were dissolved in 1:1 MEK:chloroform. Saran Resin F120 (available from Aldrich Chemical Company, Milwaukee, Wis., 30 mg) dissolved in methyl ethyl ketone (0.3 mL) was added to the resultant solution.

These coating fluids were separately coated on to poly(ethylene terephthalate) base of 4 mil (101 µm) in thickness (ICI Type 3295, supplied by ICI Americas, Inc., Wilmington Del.) using a number 18 coating rod to form Films A and B respectively.

Film A was exposed through the polyester base to infra-red radiation from a GaAlAs semiconductor diode laser in the same way as in Example 33 above. Following the infra-red exposure, the entire coated side of Film A was exposed to the unfiltered output of a low pressure mercury UV lamp, model B-100 (supplied by Black Light Eastern, a division of Spectronics Corporation, Westbury, Long Island, N.Y.) for 47 seconds. Film A was next heated on a hotplate at 117° C. for 15 seconds, after which it was laminated at 240° F. (116° C.) and 60 psi (0.4 MPa) to Film B, with the two coated sides in contact. Table 2 below shows the green optical densities achieved for various infra-red exposures; these densities were measured using an X-Rite 310 photographic densitometer, supplied by X-Rite, Inc., Grandville, Mich., with the appropriate filter.

TABLE 2

| Scanning speed (m/sec) | Green optical density |
| --- | --- |
| No IR exposure | 0.07 |
| 2.0 | 2.68 |
| 2.5 | 2.81 |
| 3.0 | 2.73 |
| 3.5 | 2.69 |
| 4.0 | 2.95 |

From the data in Table 2, it will be seen that the green optical density achieved in the imaged areas was independent of the scanning speed within the range shown in Table 2. Further experiments indicated that at higher scanning speeds, very little magenta dye density developed, presumably because so little superacid was generated during the infra-red irradiation that, even after the ultra-violet irradiation, the quantity of superacid generated did not exceed the threshold required to protonate all the infra-red dye and hence leave unbuffered superacid present in the infra-red exposed areas. Accordingly, at these high scanning speeds, even in the infra-red exposed areas, there was no unbuffered superacid available to catalyze the decomposition of the acid generator, so little or no production of the second acid took place and little magenta color developed.

Further experiments also indicated that if the ultra-violet exposure was less than 40 or more than 55 seconds, no significant difference in optical density was seen between the areas which had received infra-red irradiation and those which had not; if the ultra-violet irradiation was too short, little or no dye density developed in any part of the film, while if the ultra-violet irradiation was too long, the whole film developed the maximum dye density. Presumably, if the ultra-violet irradiation is too short and thus too little superacid precursor is decomposed during this irradiation, even in infra-red exposed areas the quantity of superacid present following the ultra-violet irradiation will not exceed the aforementioned threshold, no unbuffered superacid will be present in the infra-red exposed areas during the heating step, no acid amplification will occur, and little or no magenta dye density will result. On the other hand, if the ultra-violet irradiation is too long and thus too much superacid precursor is decomposed during this irradiation, even in areas not exposed to infrared radiation the quantity of superacid present following the ultra-violet irradiation will exceed the aforementioned threshold, unbuffered superacid will be present throughout the film and acid amplification and dye color change will occur in all areas.

EXAMPLE 35

Imaging process of the invention using a single sheet medium

This Example illustrates an imaging process of the invention generally similar to that in Example 34 above, but in which the imaging medium comprises a single sheet rather than two sheets which are laminated together following the ultra-violet irradiation.

Two dispersions were prepared as follows:
Dispersion A:

De-ionized water (60 mL) was added dropwise to a magnetically stirred solution of a surfactant (Aerosol TR-70, adjusted with potassium hydroxide to pH 6, 0.65 g), the leuco dye used in Example 34 above (2.5 g), a base (HALS-62, supplied by Fairmount Chemical Company, 0.25 g) and a polymeric binder (Elvacite 2043, supplied by DuPont de Nemours, Wilmington, Del., 2.75 g) in dichloromethane (46 mL). The resultant, very viscous mixture was sonicated, causing the viscosity to decrease, and then the mixture was allowed to stir overnight at room temperature, during which time the dichloromethane evaporated. A fluorinated surfactant (FC-120, supplied by Minnesota Mining and Manufacturing Corporation, St. Paul, Minn., 56 mg of a 25% aqueous solution) was then added.
Dispersion B:

De-ionized water (53.5 mL) was added dropwise to a magnetically stirred solution of a surfactant (Aerosol TR-70, adjusted with potassium hydroxide to pH 6, 0.58 g), a base (HALS-63, supplied by Fairmount Chemical Company, 2.45 g) and a polymeric binder (Elvacite 2043, supplied by DuPont de Nemours, 2.45 g) in dichloromethane (53.5 g). The resultant, very viscous mixture was sonicated, causing the viscosity to decrease, and then the mixture was allowed to stir overnight at room temperature, during which time the dichloromethane evaporated.

2 mL of Dispersion A was then combined with 1 mL of Dispersion B and poly(vinyl alcohol) (Vinol 540, supplied by Air Products Corporation, Allentown, Penn., 1 mL of 5% aqueous solution). The resultant coating fluid was then overcoated, using a number 8 coating rod, on to Film A prepared in Example 34 above.

The imaging medium thus prepared, which comprised a single sheet having both an acid-generating layer and a color-forming layer, was exposed through the polyester base to infra-red radiation from a GaAlAs laser in the same manner as in Example 33 above. Following this infra-red irradiation, the entire coating was exposed for 200 seconds, through the polyester base, to ultraviolet radiation from the aforementioned low pressure mercury UV lamp, model B-100 equipped with a 365 nm interference filter (supplied by Corion Corporation, Holliston, Mass.). The power measured at the film plane in the arrangement used was 0.3 mW/cm$^2$. The coating was then heated on a hotplate at 115° C. for 60 seconds. Table 3 below shows the green optical density achieved for various infra-red exposures, measured in the same manner as in Example 34 above.

TABLE 3

| Scanning speed (m/sec) | Green optical density |
| --- | --- |
| No IR exposure | 0.03 |
| 2.0 | 1.04 |
| 2.5 | 1.34 |
| 3.0 | 1.35 |
| 3.5 | 0.97 |
| 4.0 | 0.41 |

From the data in Table 3, it will be seen that the optical density achieved was independent of scanning speed only for scanning speeds below 3.5 m/s. Presumably, at higher scanning speeds, too little superacid precursor is decomposed during the infra-red irradiation, so that even in infra-red exposed areas the quantity of superacid present following the ultra-violet irradiation will not exceed the aforementioned threshold, little or no unbuffered superacid will be present in the infra-red exposed areas during the heating step, little or no acid amplification will occur, and a reduced magenta dye density will result.

EXAMPLE 36

Imaging process of the invention using an oxalic acid derivative as acid generator This Example illustrates an imaging process of the invention in which the imaging medium contains an oxalic acid derivative secondary acid generator which amplifies the unbuffered superacid present in infra-red exposed areas following the infra-red and ultra-violet irradiations.

Two coating fluids were prepared as follows:
Fluid A 1-Vinylpyrene (20 mg), the infra-red dye IR1 described in Example 33 above (3 mg), (4-n-octyloxyphenyl)phenyliodonium hexafluoroantimonate (25 mg), 2,2-dimethyl-1-[4-methoxybenzyloxalyloxy]prop- 3-yl-[4-methoxybenzyl]oxalate (100 mg, prepared as described in Example 19 above), fluorinated surfactant FC-431 (available from Minnesota Mining and Manufacturing Co., St. Paul, Minn., 50 mg of a 2% solution in 2-butanone) and 3.5 g of a 5% w/w solution of polystyrene of molecular weight approximately 45,000 (available from Aldrich Chemical Company, Milwaukee, Wis.) in 2-butanone were combined.

Fluid B De-ionized water (40 mL) was added dropwise to a magnetically stirred solution of a surfactant (Aerosol TR-70, supplied by American Cyanamid Co., Wayne, N.J.

07470, adjusted with potassium hydroxide to pH 6, 0.34 g), indicator dye 3,3-bis-[1-butyl-2-methyl-1H-indol-3-yl]-1-isobenzofuranone (sold commercially under the tradename Copikem 20 by Hilton Davis Co., 2235 Langdon Farm Road, Cincinnati, Ohio 45237, 2.0 g), a hindered amine base (Tinuvin 292, available from Ciba-Geigy Co., Ardsdale, N.Y., 0.25 g) and a polymeric binder (Elvacite 2043, available from E. I. DuPont de Nemours, Wilmington, Del., 2.5 g) in dichloromethane (40 mL). The resultant mixture was sonicated, and became very viscous; further sonication caused its viscosity to decrease (more deionized water was added during sonication), and the sonicated mixture was then passed through a microfluidizer. Residual dichloromethane was removed under reduced pressure to give a final dispersion 5.3% in solids. This dispersion below was diluted with 20% of its own weight of a 7.3% solution of poly(vinyl alcohol) (Vinol 540, supplied by Air Products Corporation, Allentown, Penn.; this material was dialyzed before use) in water.

An imaging medium was prepared by coating Fluid A on to a reflective base of 6 mil (152 μm) thickness (ICI Melinex, available from ICI Americas, Inc., Wilmington, Del.) using a #6 coating rod, followed by Fluid B, which was coated onto the dried coating of Fluid A with a #5 coating rod.

The imaging medium thus prepared was imagewise exposed to infra-red radiation form a GaAlAs semiconductor diode laser in the same way as in Example 33 above. Following the infra-red exposure, the entire film was exposed to ultraviolet radiation from a 1000 W mercury vapor lamp (filtered to remove wavelengths below about 330 nm) in a nuArc 26-1K UV exposure system (available from nuArc company, Inc., 6200 W. Howard St., Niles, Ill. 60648). The irradiance at the film plane was 16 mJ/cm$^2$, measured using a "Light Bug" radiometer, type IL390B, available from International Light, Inc., Newburyport, Mass. 01950. Regions of the film which had been exposed at 2.0, 2.5, 3.0, 3.5, 4.0 and 5.0 meters/second exhibited the same green optical density, as measured using an X-Rite 310 photographic densitometer, supplied by X-Rite, Inc., Grandville, Mich., with the appropriate filter. This density, designated $D_{max}$, was 1.10. Regions of the film which had not been exposed to infra-red radiation exhibited a green density ($D_{min}$) of 0.18.

From the foregoing, it will be seen that the present invention provides a process for generation of a superacid (and optionally a strong second acid) using radiation of wavelengths (preferably near infra-red wavelengths) to which conventional superacid precursors are not sensitive. The superacid or second acid thus generated can be used to carry out any acid-dependent reaction for which superacids and other acids have hitherto been used. In particular, preferred embodiments of the invention permit the production of high resolution images using infra-red lasers, with high sensitivity of the imaging medium.

We claim:

1. An imaging medium comprising:
   a superacid precursor; and
   a dye capable of absorbing actinic radiation of a first wavelength,
   the superacid precursor being decomposed to form a superacid by actinic radiation of a second wavelength shorter than the first wavelength in the absence of the dye, but not being decomposed by actinic radiation of the first wavelength in the absence of the dye, the superacid precursor being decomposed by actinic radiation of the first wavelength in the presence of the dye, the superacid produced by decomposition of the superacid precursor in the presence of the dye being capable of forming a protonated product derived from the dye; and
   a secondary acid generator capable of being thermally decomposed to form a secondary acid, the thermal decomposition of the secondary acid generator being catalyzed in the presence of the superacid.

2. An imaging medium according to claim 1 further comprising a polymeric binder in which the superacid precursor and the dye are dispersed.

3. An imaging medium according to claim 1 wherein the dye is a squarylium dye.

4. An imaging medium according to claim 1 wherein the superacid precursor comprises an iodonium compound.

5. An imaging medium according to claim 1 wherein the secondary acid generator is a 3,4-disubstituted-cyclobut-3-ene-1,2-dione in which at least one of the 3- and 4-substituents consists of an oxygen atom bonded to the squaric acid ring, and an alkyl or alkylene group, a partially hydrogenated aryl or arylene group, or an aralkyl group bonded to said oxygen atom, said 3,4-disubstituted-cyclobut-3-ene-1,2-dione being capable of decomposing so as to cause replacement of the or each original alkoxy, alkyleneoxy, aryloxy, aryleneoxy or aralkyloxy group of the derivative with a hydroxyl group.

6. An imaging medium according to claim 5 wherein the 3,4-disubstituted-cyclobut-3-ene-1,2-dione is selected from the group consisting of:
   (a) primary and secondary esters of squaric acid in which the α-carbon atom bears a non-basic cation-stabilizing group;
   (b) tertiary esters of squaric acid in which the α-carbon atom does not have an sp$^2$ or sp hybridized carbon atom directly bonded thereto; and
   (c) tertiary esters of squaric acid in which the α-carbon atom does have an sp$^2$ or sp hybridized carbon atom directly bonded thereto, provided that this sp$^2$ or sp hybridized carbon atom, or at least one of these sp$^2$ or sp hybridized carbon atoms, if more than one such atom is bonded directly to the α-carbon atom, is conjugated with an electron-withdrawing group.

7. An imaging medium according to claim 5 wherein the 3,4-disubstituted-cyclobut-3-ene-1,2-dione is of one of the following formulae:

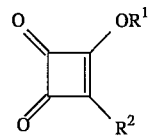

a.

in which $R^1$ is an alkyl group, a partially hydrogenated aromatic group, or an aralkyl group, and $R^2$ is a hydrogen atom or an alkyl, cycloalkyl, aralkyl, aryl, amino, acylamino, alkylamino, dialkylamino, alkylthio, alkylseleno, dialkylphosphino, dialkylphosphoxy or trialkylsilyl group, subject to the proviso that either or both of the groups $R^1$ and $R^2$ may be attached to a polymer;

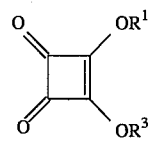

b.

in which $R^1$ and $R^3$ independently are each an alkyl group, a partially hydrogenated aryl group or an aralkyl group, subject to the proviso that either or both of the groups $R^1$ and $R^3$ may be attached to a polymer; and

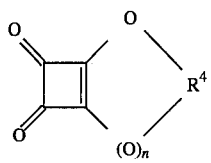

in which n is 0 or 1, and $R^4$ is an alkylene group or a partially hydrogenated arylene group; or the squaric acid derivative comprises at least one unit of the formula:

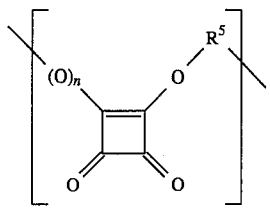

in which n is 0 or 1, and $R^5$ is an alkylene or partially hydrogenated arylene group.

8. An imaging medium according to claim 1 wherein the secondary acid generator is an oxalic acid diester and the secondary acid generated therefrom is oxalic acid or an oxalic acid monoester having one carboxyl group.

9. An imaging medium according to claim 8 wherein the oxalic acid diester is selected from the group consisting of:
    (a) primary and secondary esters of oxalic acid in which the α-carbon atom bears a non-basic cation-stabilizing group;
    (b) tertiary esters of oxalic acid in which the α-carbon atom does not have an $sp^2$ or sp hybridized carbon atom directly bonded thereto;
    (c) tertiary esters of oxalic acid in which the α-carbon atom does have an $sp^2$ or sp hybridized carbon atom directly bonded thereto, provided that this $sp^2$ or sp hybridized carbon atom, or at least one of these $sp^2$ or sp hybridized carbon atoms, if more than one such atom is bonded directly to the α-carbon atom, is conjugated with an electron-withdrawing group;
    (d) an ester formed by condensation of two moles of an alcohol with the bis(hemioxalate) of a diol, provided that the ester contains at least one ester grouping of type (a), (b) or (c);
    (e) polymeric oxalates derived from polymerization of oxalate esters having an ethylenically unsaturated group, provided that the ester contains at least one ester grouping of type (a), (b) or (c); and
    (f) condensation polymers of oxalates, provided that the ester contains at least one ester grouping of type (a), (b) or (c) above.

10. An imaging medium according to claim 8 wherein the oxalic acid diester is one which begins to decompose thermally at a temperature in the range of about 140° to about 180° C., as measured by differential scanning calorimetry in a nitrogen atmosphere at a 10° C./minute temperature ramp, in the absence of any catalyst.

11. An imaging medium according to claim 1 further comprising an acid-sensitive material capable of changing color in the presence of the secondary acid.

12. An imaging medium according to claim 11 wherein the acid-sensitive material is in admixture with an amount of a basic material insufficient to neutralize all the secondary acid capable of being liberated by heating of the secondary acid generator.

13. An imaging medium according to claim 12 wherein the acid-sensitive material is present in a layer or phase separate from the layer or phase containing the superacid precursor and the secondary acid generator.

14. An imaging medium comprising:
    a superacid precursor and an infra-red dye capable of absorbing infra-red radiation having a wavelength within the range of about 700 to about 1200 nm, the superacid precursor being capable of being decomposed by ultraviolet radiation having a wavelength in the range of about 180 to about 400 nm to form a superacid, the superacid precursor not being decomposed by infra-red radiation having a wavelength within the range of about 700 to about 1200 nm in the absence of the infra-red dye.

15. An imaging medium according to claim 14 further comprising at least one of:
    (a) a secondary acid generator capable of acid-catalyzed decomposition by the unbuffered superacid to form a secondary acid;
    (b) a monomer or oligomer which polymerizes in the presence of the unbuffered superacid;
    (c) a polymer which depolymerizes in the presence of the unbuffered superacid;
    (d) a polymer the solubility of which in a solvent changes in the presence of the unbuffered superacid; and
    (e) a polymer the adhesion of which to a material changes in the presence of the unbuffered superacid.

16. An imaging medium according to claim 14 further comprising a polymeric binder in which the superacid precursor and the infra-red dye are dispersed.

* * * * *